US012631645B2

(12) United States Patent
Srivastava et al.

(10) Patent No.: US 12,631,645 B2
(45) Date of Patent: May 19, 2026

(54) DETECTION OF BCL-2 FAMILY HETERODIMER COMPLEXES AND USE THEREOF

(71) Applicant: The U.S.A., as represented by the Secretary, Department of Health and Human Services, Bethesda, MD (US)

(72) Inventors: Apurva Kumar Srivastava, Frederick, MD (US); Dominic Esposito, Middletown, MD (US); Jeevan Prasaad Govindharajulu, Frederick, MD (US); Ralph Ewin Parchment, Frederick, MD (US); James Halpern Doroshow, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1274 days.

(21) Appl. No.: 17/422,972

(22) PCT Filed: Jan. 29, 2020

(86) PCT No.: PCT/US2020/015694
§ 371 (c)(1),
(2) Date: Jul. 14, 2021

(87) PCT Pub. No.: WO2020/160157
PCT Pub. Date: Aug. 6, 2020

(65) Prior Publication Data
US 2022/0074944 A1 Mar. 10, 2022

Related U.S. Application Data

(60) Provisional application No. 62/798,615, filed on Jan. 30, 2019.

(51) Int. Cl.
*G01N 33/53* (2006.01)
*G01N 33/543* (2006.01)
*G01N 33/575* (2026.01)

(52) U.S. Cl.
CPC ... *G01N 33/5759* (2026.01); *G01N 33/54313* (2013.01); *G01N 2333/705* (2013.01)

(58) Field of Classification Search
None
See application file for complete search history.

(56) References Cited

U.S. PATENT DOCUMENTS

| | | | |
|---|---|---|---|
| 5,989,924 A | 11/1999 | Root et al. | |
| 2009/0181410 A1* | 7/2009 | Hsieh | C07K 16/18 |
| | | | 530/391.3 |
| 2009/0280510 A1 | 11/2009 | Cardone et al. | |

| | | | |
|---|---|---|---|
| 2016/0178634 A1 | 6/2016 | Cardone | |
| 2018/0180610 A1* | 6/2018 | Taha | G01N 33/56911 |
| 2018/0208672 A1* | 7/2018 | Cardone | C07K 16/18 |
| 2018/0303815 A1* | 10/2018 | Merchant | A61K 31/496 |
| 2020/0348280 A1* | 11/2020 | Cardone | C07K 16/005 |

FOREIGN PATENT DOCUMENTS

WO WO 2015/017788 2/2015

OTHER PUBLICATIONS

Leverson et al., Potent and selective small-molecule MCL-1 inhibitors demonstrate on-target cancer cell killing activity as single agents and in combination with ABT-263 (navitoclax), Cell Death and Disease, 2015, 6, pp. 1-11. (Year: 2015).*
Kohl et al., Immunometric Antibody Sandwich Enzyme-Linked Immunosorbent Assay, Cold Spring Harb Protoc; Jul. 21, 2018, pp. 450-457. (Year: 2018).*
Xiao et al., MCL-1 is a key determinant of breast cancer cell survivial: validation of MCL-1 dependency utilizing a highly selective small molecule inhibitor, Mol Cancer Ther; 14(8) Aug. 2015, pp. 1837-1847, (Year: 2015).*
Shih et al., An enzyme-linked immunosorbent assay on a centrifugal platform using magnetic beads, Biomicrofluidics, 9, 052110, 2014, pp. 1-11. (Year: 2014).*
Bai et al., "Small-Molecule SMAC Mimetics as New Cancer Therapeutics," *Pharmacol. Ther.*, vol. 144:82-95, 2014.
Balakrishnan et al., "Gossypol, a BH3 Mimetic, Induces Apoptosis in Chronic Lymphocytic Leukemia Cells," *Blood*, vol. 112:1971-1980, 2008.
Kale et al., "BCL-2 Family Proteins: Changing Partners in the Dance towards Death," *Cell Death Differ.*, vol. 25:65-80, 2018.
International Search Report and Written Opinion, dated Apr. 29, 2020, for PCT/US2020/015694 (12 pages).
Reyna et al., "Direct Activation of BAX by BTSA1 Overcomes Apoptosis Resistance in Acute Myeloid Leukemia," *Cancer Cell*, vol. 32:490-505, 2017.
Shamas-Din et al., "Mechanisms of Action of BcL-2 Family Proteins," *Cold Spring Harb. Perspect. Biol.*, vol. 5, 2013 (21 pages).
Srivastava et al., "Effect of a Smac Mimetic (TL32711, Birinapant) on the Apoptotic Program and Apoptosis Biomarkers Examined with Validated Multiplex Immunoassays Fit for Clinical Use," *Clin. Cancer Res.*, vol. 22:1000-1010, 2016.
Srivastava et al., "Abstract 4920: Intratumoral Levels of BAX-BAK Heterodimer as a Specific On-Target Pharmacodynamic Biomarker of Drug Action by Novel BH3 Mimetics," Proceedings: AACR Annual Meeting, Apr. 14-18, 2018, Chicago, IL, published Jul. 2018 (4 pages).

(Continued)

*Primary Examiner* — Gary Counts
(74) *Attorney, Agent, or Firm* — Klarquist Sparkman, LLP

(57) ABSTRACT

Immunoassays to detect the presence of Bcl-2 family heterodimeric complexes are described. The immunoassays are designed to detect one or more of BIM-Bcl-2, BIM-Bcl-xL, BIM-Mcl-1 and BAX BAK heterodimers. The assays can be used, for example, to select a BH3 mimetic, or other drug targeting the apoptosis pathway, that is effective for treating a specific cancer, or to select a subject who is likely to respond to a particular BH3 mimetic.

20 Claims, 24 Drawing Sheets
Specification includes a Sequence Listing.

(56) References Cited

OTHER PUBLICATIONS

Srivastava et al., "Poster 4920: Intratumoral Levels of BAX-BAK Heterodimer as a Specific On-Target Pharmacodynamic Biomarker of Drug Action by Novel BH3 Mimetics," poster presentation at the AACR Annual Meeting, Apr. 17, 2018.

Srivastava et al., "BAX-BAK heterodimer as a pharmacodynamic biomarker of on- target drug action of Mcl-1 inhibitors to evaluate in-vivo effectiveness," poster presentation at the American Society of Clinical Oncology (ASCO) meeting, May 31-Jun. 4, 2018.

Srivastava et al., "Progress on Development of a Multiplex Panel of 15 Biomarkers to Support the Development of Anticancer Drugs Targeting Apoptosis," Poster, Abstract #3359, 2013.

Ukrainskaya et al., "Death Receptors: New Opportunities in Cancer Therapy," *Acta Naturae*, vol. 9:55-63, 2017.

Wolf, "BH3 Mimetics for the Treatment of Prostate Cancer," *Front. Pharmacol.*, vol. 8, 2017 (7 pages).

* cited by examiner

FIG. 1

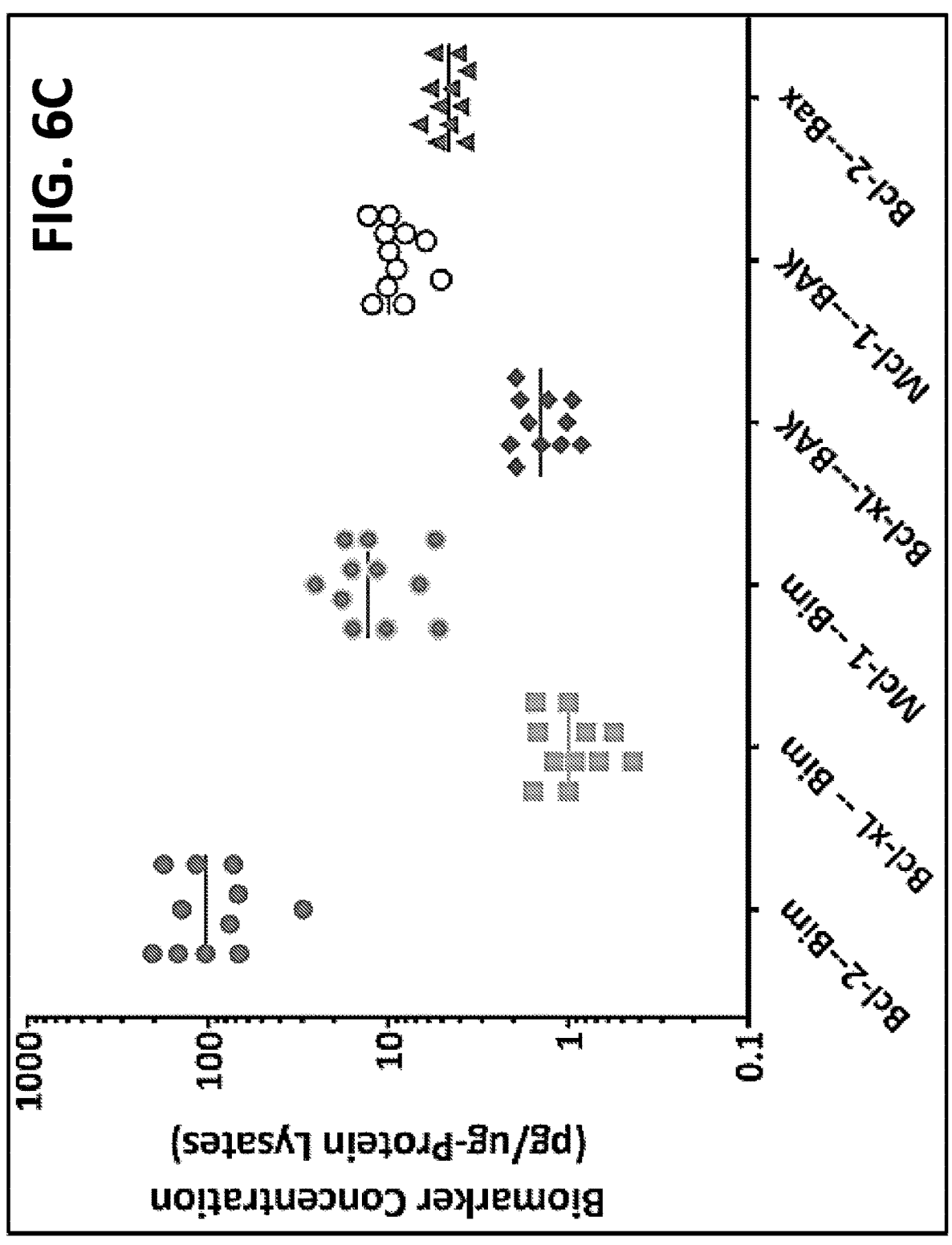

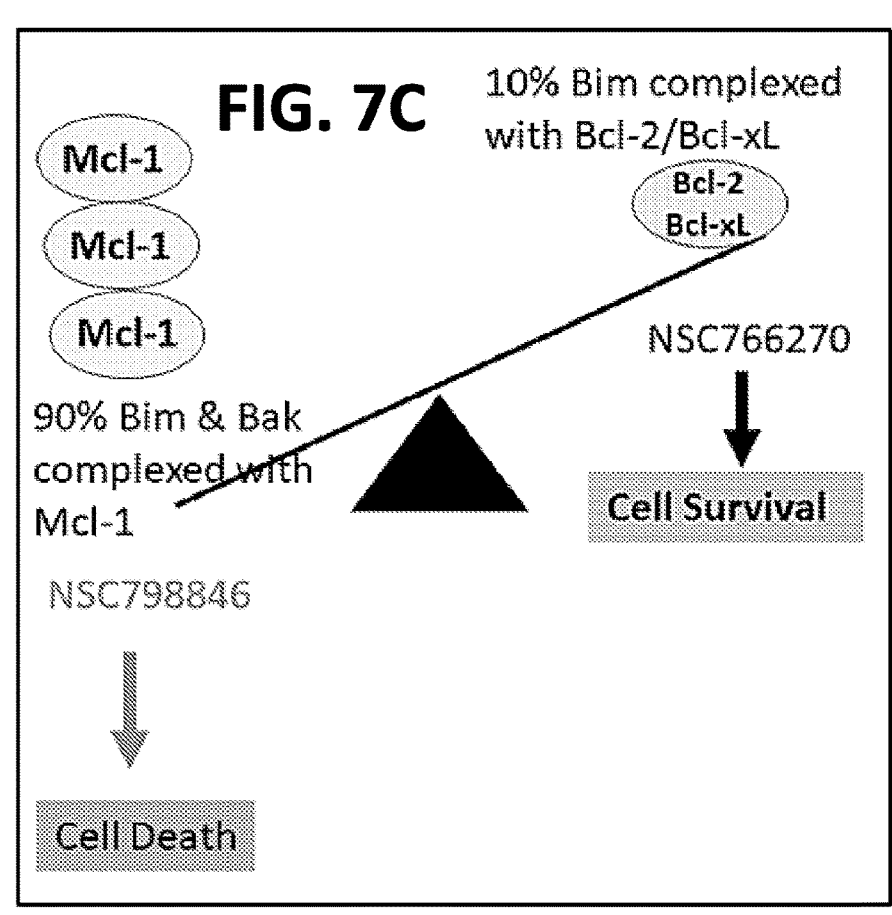
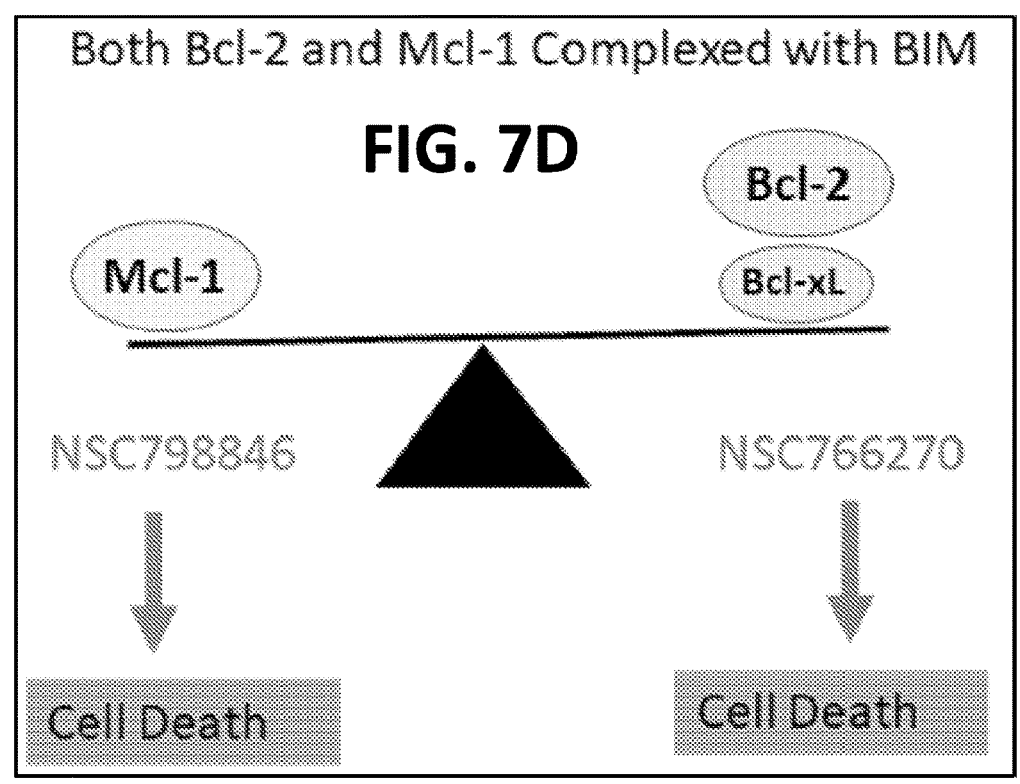

DETECTION OF BCL-2 FAMILY HETERODIMER COMPLEXES AND USE THEREOF

CROSS REFERENCE TO RELATED APPLICATIONS

This application is the U.S. National Stage of International Application No. PCT/US2020/015694, filed Jan. 29, 2020, which was published in English under PCT Article 21(2), which claims the benefit of U.S. Provisional Application No. 62/798,615, filed Jan. 30, 2019. The above-listed applications are herein incorporated by reference in their entirety.

ACKNOWLEDGMENT OF GOVERNMENT SUPPORT

This invention was made with government support under contract number HHSN261200800001E awarded by the National Institutes of Health. The government has certain rights in the invention.

FIELD

This disclosure concerns an immunoassay for the detection of Bcl-2 family member heterodimeric complexes, and use of the immunoassay, such as for determining the effectiveness of a drug targeting the apoptosis pathway in a subject with cancer.

BACKGROUND

Anti-apoptotic Bcl-2 protein family members are overexpressed in up to 30% of all cancers, providing cancer cells a pro-survival advantage to evade cell death, grow and proliferate. Consequently, several agents are under investigation as potential anti-cancer therapeutics for interventional therapy, for example, the Bcl-2 inhibitor venetoclax (FDA approved in 2016), the Bcl-xL inhibitor novitoclax, and the Mcl-1 inhibitor S63845. These agents act by binding tightly to anti-apoptotic proteins Bcl-2, Bcl-xL, and Mcl-1 and disengaging them from pro-apoptotic BIM, BAX, and BAK proteins. Once the pro-apoptotic proteins are relieved, they are activated, resulting in formation of mitochondrial pores, activation of caspases, and induction of apoptosis.

Current strategies for selecting patients who will receive treatment with drugs targeting the apoptosis pathway, such as BH3 mimetics, include measurement of Bcl-2 family member proteins by immunohistochemistry (IHC), which allows for qualitative measurement of a protein, but not measurement of protein-protein interactions. Another current screening method involves measurement of nucleic acid sequences that encode Bcl-2, Mcl-1, Bcl-xL, or other apoptosis pathway targets. Similar to IHC, this method measures mRNA levels irrespective of the translated proteins and their interactions with other Bcl-2 family member proteins. A third approach includes isolating tumor cells, culturing the cells in vitro, and challenging the cultured tumor cells with synthetic peptides to identify which BH3 mimetic is most effective for inducing cell death.

A need exists for improved methods to detect functional protein-protein interactions of Bcl-2 family members and to evaluate the effectiveness of anti-cancer drugs.

SUMMARY

Described herein are methods of detecting Bcl-2 family heterodimeric complexes in biological samples, such as for aiding in the selection of a cancer patient who is likely to respond to a drug targeting the apoptosis pathway, or for selecting a drug (such as a BH3 mimetic) that will be effective for treating a patient diagnosed with cancer.

Provided herein is a method of detecting a Bcl-2 family heterodimeric complex in a biological sample. In some embodiments, the method includes providing a cell lysate of a biological sample that comprises cells; and detecting the presence of a heterodimeric Bcl-2 family protein complex in the cell lysate, wherein the heterodimeric complex comprises a first protein and a second protein, and wherein the heterodimeric complex is selected from the group consisting of BIM-Bcl-2, BIM-Bcl-xL, BIM-Mcl-1 and BAX-BAK. In some embodiments, detecting the heterodimeric complex includes providing an antibody specific for the first protein bound to a solid support; providing a detection antibody specific for the second protein; contacting the cell lysate with the antibody-bound solid support and the detection antibody; and detecting the presence of the detection antibody.

Also provided is a method of selecting a subject diagnosed with cancer as suitable for treatment with a drug targeting the apoptosis pathway. In some embodiments, the method includes providing a biological sample obtained from the subject, wherein the biological sample comprises cancer cells; preparing a cell lysate from the cells of the biological sample; and detecting Bcl-2 family heterodimeric complexes in the cell lysate in the presence and absence of the drug, wherein the heterodimeric complexes comprise a first protein and a second protein, and wherein the heterodimeric complexes are selected from the group consisting of BIM-Bcl-2, BIM-Bcl-xL, BIM-Mcl-1 and BAX-BAK. In some embodiments, detecting the Bcl-2 family heterodimeric complexes includes providing an antibody specific for the first protein bound to a solid support; providing a detection antibody specific for the second protein; contacting the cell lysate with the antibody-bound solid support and the detection antibody; and detecting the presence of the detection antibody. A decrease in BIM-Bcl-2, BIM-Bcl-xL and/or BIM-Mcl-1 heterodimeric complexes, or an increase in BAX-BAK heterodimeric complexes, in the presence of the drug compared to in the absence of the drug, indicates the subject is suitable for treatment with the drug.

Further provided is a method to select a drug targeting the apoptosis pathway that is effective for treating cancer in a subject. In some embodiments, the method includes providing a biological sample obtained from the subject, wherein the biological sample comprises cancer cells; preparing a cell lysate from the cancer cells of the biological sample; and detecting Bcl-2 family heterodimeric complexes in the cell lysate in the presence and absence of a candidate drug targeting the apoptosis pathway, wherein the heterodimeric complexes comprise a first protein and a second protein, and wherein the heterodimeric complexes are selected from the group consisting of BIM-Bcl-2, BIM-Bcl-xL, BIM-Mcl-1 and BAX-BAK. In some embodiments, detecting the Bcl-2 family heterodimeric complexes includes providing an antibody specific for the first protein bound to a solid support; providing a detection antibody specific for the second protein; contacting the cell lysate with the antibody-bound solid support and the detection antibody; and detecting the presence of the detection antibody. A decrease in BIM-Bcl-2, BIM-Bcl-xL and/or BIM-Mcl-1 heterodimeric complexes, or an increase in BAX-BAK heterodimeric complexes, in the presence of the candidate drug targeting the apoptosis pathway compared to in the absence of the drug, indicates the candidate drug targeting the apoptosis pathway is effective for treating the cancer.

The foregoing and other objects and features of the disclosure will become more apparent from the following detailed description, which proceeds with reference to the accompanying figures.

BRIEF DESCRIPTION OF THE DRAWINGS

FIG. 1 is a schematic depiction of apoptosis pathways and Bcl-2 family protein interactions that regulate cell death. Overexpression of anti-apoptotic proteins of the Bcl-2 and IAP families is common in the pathogenesis and progression of malignancies, making these protein families two of the most highly validated classes of anticancer targets. Bcl-2 family inhibitors (such as Venetoclax and Novitoclax) and Mcl-1 inhibitors (such as S64315, MIK665 and AMG176) are classified as BH3 mimetics; they target specific anti-apoptotic proteins to reverse resistance to cell death. BH3 mimetics act by disrupting heterodimeric complexes comprised of an anti-apoptotic protein (such as Bcl-2 Bcl-xL or Mcl-1) and a pro-apoptotic protein (such as Puma, Noxa, BAD, BMF, BID, BIM, Bax and Bak).

(FIG. 2A) The quantity of BIM-Mcl-1, BIM-Bcl-xL, BAK-Mcl-1 and BAK-Bcl-xL heterodimers in the mitochondrial fraction of various cancer cell lines. The quantity of heterodimer is measured in ng per 500 μg of total protein. (FIG. 2B) The quantity of Bcl-2-BIM, Bcl-xL-BIM, Mcl-1-BIM, BAX-BAK, Bcl-xL-BAK, Mcl-1-BAK, BAX-Bcl-2 heterodimers in the mitochondrial fraction of cancer cell lines AMO-1 and MV411. In cell lines that are sensitive to Mcl-1 inhibitor (such as AMO-1 cells), the majority of Mcl-1 was bound to BIM.

(FIG. 3A) BIM-Mcl-1 heterodimer levels in AMO-1 and MV411 cell lines treated with Mcl-1 inhibitor S63845 (798846) or Bcl-xL inhibitor Novitoclax (759659). BIM-Mcl-1 concentrations were 80- to 90-fold higher in AMO-1 cells compared to MV411 cells. In addition, BIM-Mcl-1 levels were decreased by S63845 treatment, but largely unaffected by treatment with Novitoclax. (FIG. 3B) BAX-BAK heterodimer levels in AMO-1 and MV411 cell lines treated with S63845 (798846) or Novitoclax (759659). The results show that inhibition of BIM-Mcl-1 complexes caused increased downstream activation of BAX-BAK heterodimer formation in the mitochondrial fraction. (FIG. 3C) Cleaved caspase-3 levels in AMO-1 and MV411 cancer cell lines treated with S63845 (798846) or Novitoclax (759659). The results demonstrate that increased activation of BAX-BAK heterodimers leads to cleavage of caspase-3.

(FIG. 4A) BIM-Bcl-xL levels in HCT116 and MOLT-4 tumor cell lines. BIM-Bcl-xL levels were only disrupted by Novitoclax (759659), a known Bcl-xL inhibitor, but not by Mcl-1 inhibitor S63845 (798846). (FIG. 4B) BIM-Mcl-1 heterodimer levels in HCT116 and MOLT-4 tumor cell lines. BIM-Mcl-1 levels were only suppressed by S63845. Novitoclax treatment resulted in increased BIM-Mcl-1 levels due to re-equilibrium of BIM and Bcl-xL/Mcl-1. (FIG. 4C) BAX-BAK heterodimer levels in HCT116 and MOLT-4 tumor cell lines. Both S63845 and Novitoclax increased downstream effector BAX-BAK levels. (FIG. 4D) Levels of cleaved caspase-3 in HCT116 and MOLT-4 tumor cell lines. Both drugs increased activation of cleaved caspase-3 and apoptotic cell death.

(FIG. 5A) Schematic showing the downstream effect of BH3 mimetics on BIM-Bcl-xL, BIM-Mcl-1 and BIM-Bcl-2 heterodimeric complexes and apoptosis induction. (FIG. 5B) BIM-Bcl-xL, BIM-Mcl-1, BIM-Bcl-2, BAX-BAK and cleaved caspase-3 levels in the cell lysate of AMO-1 cells treated with Mcl-1 inhibitor S63845. Treatment with S63845 led to a decrease in BIM-Mcl-1 heterodimers and an increase in both BAX-BAK heterodimers and cleaved caspase-3. (FIG. 5C) BIM-Bcl-xL, BIM-Mcl-1, BIM-Bcl-2, BAX-BAK and cleaved caspase-3 levels in the cell lysate of AMO-1 cells treated with Bcl-xL inhibitor Novitoclax. Treatment with Novitoclax did not lead to a significant increase in caspase-3 cleavage due to the lack of BIM-Bcl-xL heterodimeric complexes in AMO-1 cells. (FIG. 5D) BIM-Bcl-xL, BIM-Mcl-1, BIM-Bcl-2, BAX-BAK and cleaved caspase-3 levels in the cell lysate of Mv4-11 cells treated with Mcl-1 inhibitor S63845. Treatment with S63845 led to a significant decrease in BIM-Mcl-1 heterodimers and a significant increase in both BAX-BAK heterodimers and cleaved caspase-3. (FIG. 5E) BIM-Bcl-xL, BIM-Mcl-1, BIM-Bcl-2, BAX-BAK and cleaved caspase-3 levels in the cell lysate of Mv4-11 cells treated with Bcl-xL inhibitor Novitoclax. Treatment with Novitoclax led to a decrease in BIM-Bcl-xL heterodimeric complexes and an increase in BIM-Mcl-1, BAX-BAK and cleaved caspase-3.

FIG. 6C is a graph showing the profile of BIM complexes in peripheral blood or bone marrow of chronic lymphocytic leukemia (CLL) patients. Similar heterodimer profiles were identified in samples from all 11 patients with CLL.

(FIG. 7A) Levels of heterodimer complexes in tumor lysates collected 16 hours after treatment with 25 mg/kg of NSC798846 administered intravenously or 100 m/kg NSC766270 administered orally. Multiple myeloma model AMO-1 showed Mcl-1 dependency and treatment with Bcl-2 inhibitor NSC766270 was ineffective because BIM released from disruption of Bcl-2-BIM complexes was largely bound to Mcl-1 and did not initiate BAK-BAX oligomerization, subsequent caspase-3 activation and cell death. The disruption of Bcl-2-BIM by Mcl-1 inhibitor NSC798846 was due to overall degradation of BIM. (FIG. 7B) Heterodimer levels in tumor lysates from MV411 collected 24 hours post treatment with the indicated doses showed both Mcl-1 or Bcl-2 inhibitors were equally effective in disrupting the balance of BIM complexes and initiating caspase-3 activation and cell death.

FIGS. 7C-7D are cartoons depicting action of the two BH3 mimetics on disruption of major pro-survival protein complexes that trigger mitochondrial activation of caspase-3 and cell death.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, named 4239-101599-03_ST25.txt, created on Apr. 8, 2026, 20,134 bytes, which is incorporated by reference herein. In the accompanying sequence listing:

SEQ ID NO: 1 is the amino acid sequence of
calibrator fusion protein BIM-Bcl-2:
GAKQPSDVSSECDREGRQLQPAERPPQLRPGAPTSLQTEPQGNPEGNHG

GEGDSCPHGSPQGPLAPPASPGPFATRSPLFIFMRRSSLLSRSSSGYFS

FDTDRSPAPMSCDKSTQTPSPPCQAFNHYLSAMASMRQAEPADMRPEIW

IAQELRRIGDEFNAYYARRVFLNNYQAAEDHPRMVILRLLRYIVRLVWR

MHGSGAGGSAGGSGAGSGAGSGAHAGRTGYDNREIVMKYIHYKLSQRGY

EWDAGDVGAAPPGAAPAPGIFSSQPGHTPHPAASRDPVARTSPLQTPAA

PGAAAGPALSPVPPVVHLTLRQAGDDFSRRYRRDFAEMSSQLHLTPFTA

RGRFATVVEELFRDGVNWGRIVAFFEFGGVMCVESVNREMSPLVDNIAL

WMTEYLNRHLHTWIQDNGGWDAFVELYGPSMRPLFDFSGGSWSGPQFEK

G

SEQ ID NO: 2 is the amino acid sequence of
calibrator fusion protein BIM-Bcl-xL:
GAKQPSDVSSECDREGRQLQPAERPPQLRPGAPTSLQTEPQGNPEGNHG

GEGDSCPHGSPQGPLAPPASPGPFATRSPLFIFMRRSSLLSRSSSGYFS

FDTDRSPAPMSCDKSTQTPSPPCQAFNHYLSAMASMRQAEPADMRPEIW

IAQELRRIGDEFNAYYARRVFLNNYQAAEDHPRMVILRLLRYIVRLVWR

MHGSGAGGSAGGSGAGSGAGSGSQSNRELVVDFLSYKLSQKGYSWSQFS

DVEENRTEAPEGTESEMETPSAINGNPSWHLADSPAVNGATGHSSSLDA

REVIPMAAVKQALREAGDEFELRYRRAFSDLTSQLHITPGTAYQSFEQV

VNELFRDGVNWGRIVAFFSFGGALCVESVDKEMQVLVSRIAAWMATYLN

DHLEPWIQENGGWDTFVELYGNNAAAESRKGQERFNRGGSWSGPQFEKG

SEQ ID NO: 3 is the amino acid sequence of
calibrator fusion protein BIM-Mcl-1:
GAKQPSDVSSECDREGRQLQPAERPPQLRPGAPTSLQTEPQGNPEGNHG

GEGDSCPHGSPQGPLAPPASPGPFATRSPLFIFMRRSSLLSRSSSGYFS

FDTDRSPAPMSCDKSTQTPSPPCQAFNHYLSAMASMRQAEPADMRPEIW

IAQELRRIGDEFNAYYARRVFLNNYQAAEDHPRMVILRLLRYIVRLVWR

MHGSGAGGSAGGSGAGSGAGSGFGLKRNAVIGLNLYCGGAGLGAGSGGA

-continued

TRPGGRLLATEKEASARREIGGGEAGAVIGGSAGASPPSTLTPDSRRVA

RPPPIGAEVPDVTATPARLLFFAPTRRAAPLEEMEAPAADAIMSPEEEL

DGYEPEPLGKRPAVLPLLELVGESGNNTSTDGSLPSTPPPAEEEEDELY

RQSLEIISRYLREQATGAKDTKPMGRSGATSRKALETLRRVGDGVQRNH

ETAFQGMLRKLDIKNEDDVKSLSRVMIHVFSDGVTNWGRIVTLISFGAF

VAKHLKTINQESCIEPLAESITDVLVRTKRDWLVKQRGWDGFVEFFHVE

DLEGGIRNVLLAFAGVAGVGAGLAYLIRGGSWSGPQFEKG

SEQ ID NO: 4 is the amino acid sequence of
calibrator fusion protein BAX-BAK:
GASGQGPGPPRQECGEPALPSASEEQVAQDTEEVFRSYVFYRHQQEQEA

EGVAAPADPEMVTLPLQPSSTMGQVGRQLAIIGDDINRRYDSEFQTMLQ

HLQPTAENAYEYFTKIATSLFESGINWGRVVALLGFGYRLALHVYQHGL

TGFLGQVTRFVVDFMLHHCIARWIAQRGGWVAALNLGNGSGAGGSAGGS

GAGSGAGSGDGSGEQPRGGGPTSSEQIMKTGALLLQGFIQDRAGRMGGE

APELALDPVPQDASTKKLSECLKRIGDELDSNMELQRMIAAVDTDSPRE

VFFRVAADMFSDGNFNWGRVVALFYFASKLVLKALCTKVPELIRTIMGW

TLDFLRERLLGWIQDQGGWDGLLSYFGTGGSWSGPQFEKG

SEQ ID NO: 5 is the amino sequence of a peptide
linker:
GSGAGGSAGGSGAGSGAGSG

Figure 8A:
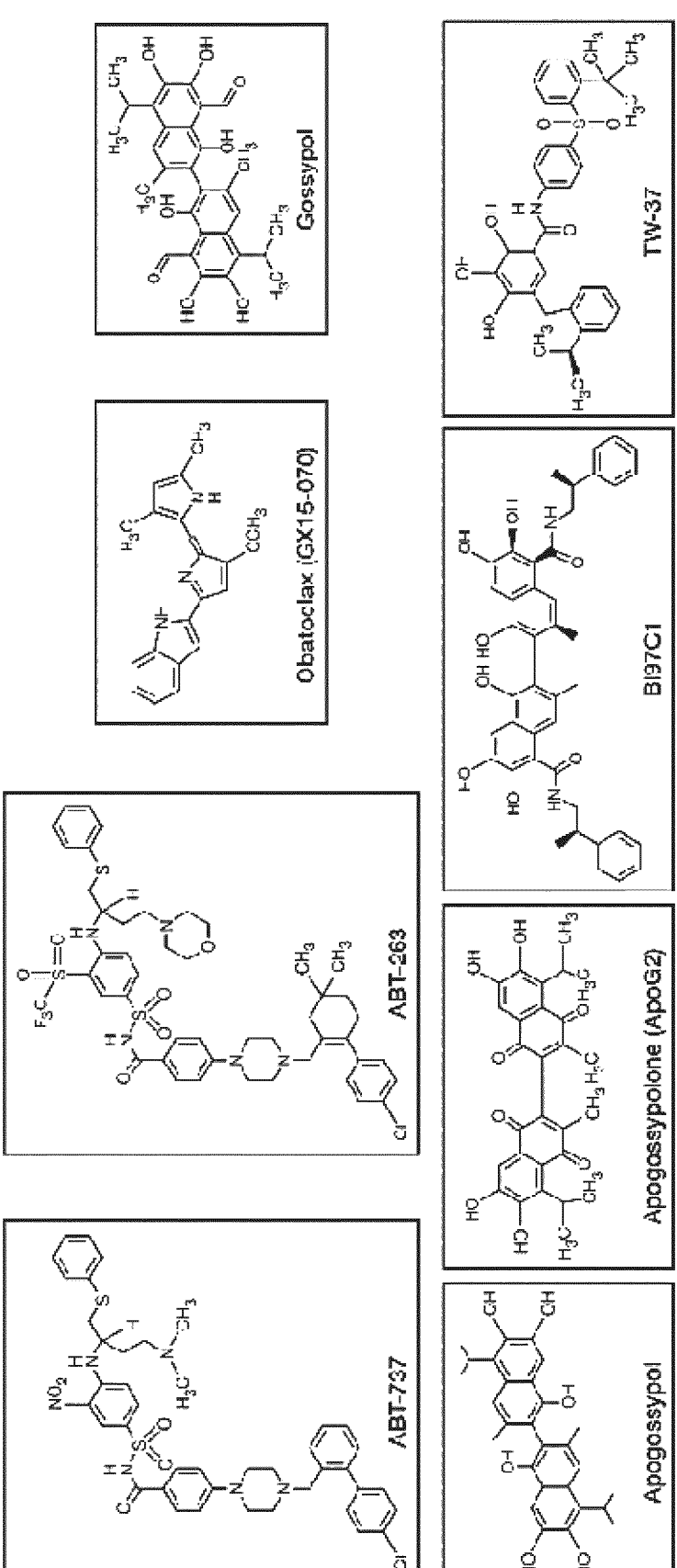
FIGS. 8A-8C are reproduced from Billard, *Mol. Cancer Ther.* 12:1691-700, 2013, herein incorporated by reference in its entirety.
Figure 8B:
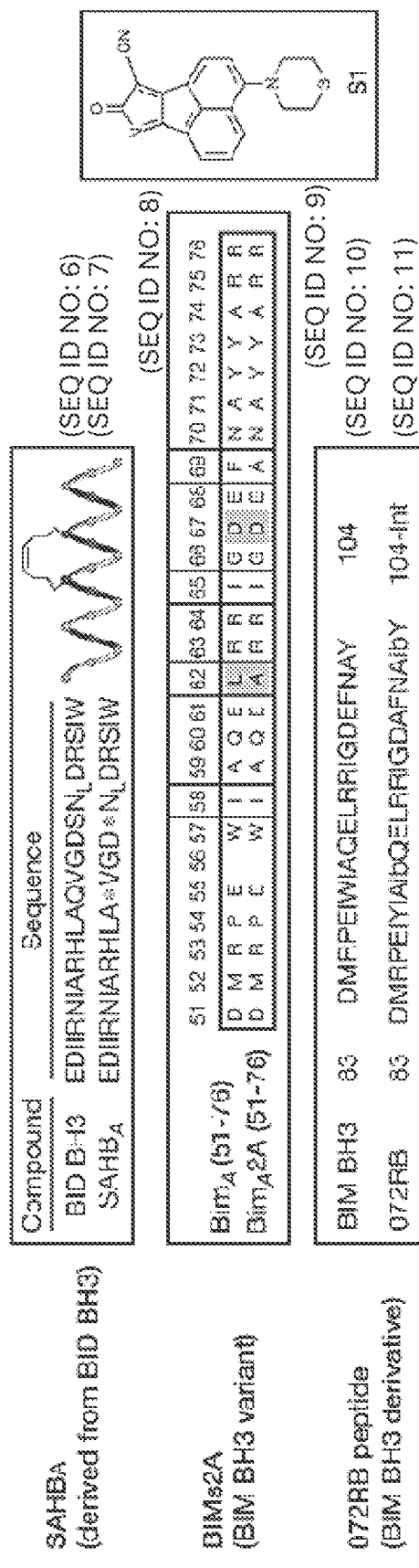
Figure 8C:
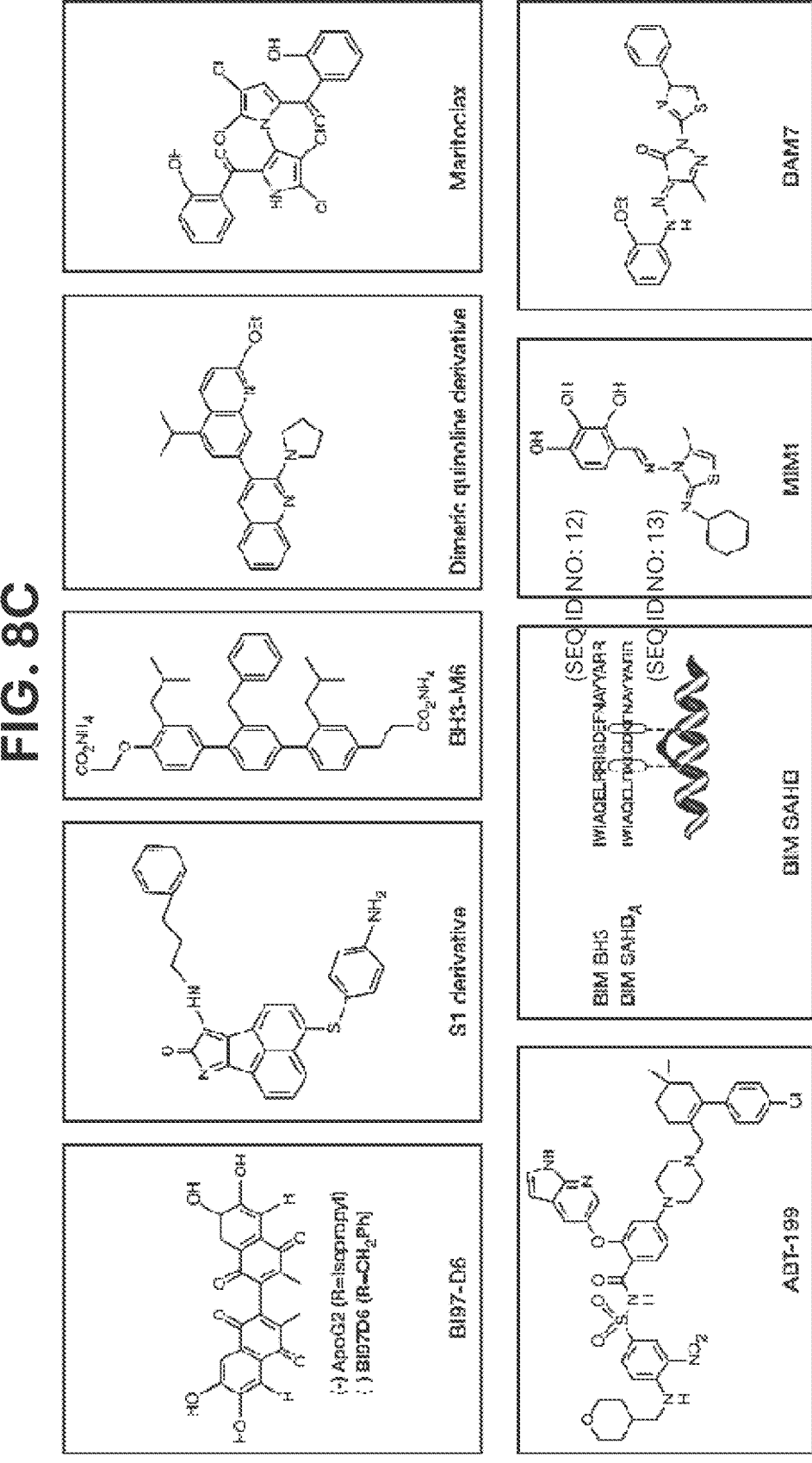

SEQ ID NOs: 6-13 are amino acid sequences shown in FIGS. 8B-8C.

DETAILED DESCRIPTION

I. Abbreviations

AML acute myeloid leukemia
BAK Bcl-1 antagonist/killer
BAX Bcl-2 associated X protein
Bcl-2 B cell lymphoma 2
Bcl-xL B cell lymphoma extra-large
BH3 Bcl-2 homology 3
BIM-Bcl-2 interacting mediator of cell death
CDK cyclin-dependent kinase
CLL chronic lymphocytic leukemia
IAP inhibitor of apoptosis protein
IHC immunohistochemistry
Mcl-1 myeloid cell leukemia 1
MM multiple myeloma

II. Terms and Methods

Unless otherwise noted, technical terms are used according to conventional usage. Definitions of common terms in molecular biology may be found in Benjamin Lewin, *Genes X*, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the term "comprises" means "includes." Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Administration: To provide or give a subject an agent, such as a drug targeting the apoptosis pathway, by any effective route. Exemplary routes of administration include, but are not limited to, injection (such as subcutaneous, intramuscular, intradermal, intraperitoneal, intratumoral, and intravenous), transdermal, intranasal, and inhalation routes.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (scFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods of this disclosure can be monoclonal or polyclonal, and for example specifically bind a target such as the target antigen. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

A "detection antibody" is an antibody that specifically binds a target analyte, such as a target protein (for example, a Bcl-2 family member protein) and is either labeled (such as with a fluorophore, radioisotope, hapten or enzyme) to provide a means for detection, or detection is based on molecular biophysical properties, such as mass spectrometry (MS), microcantilevers, quartz-crystal microbalance (QCM), surface plasmon resonance (SPR) and localized surface plasmon resonance.

BAX/BAK modulator: Any drug or compound that modulates activity of BAX and/or BAK. In some examples, the BAX/BAK modulator is a direct BAX modulator (such as an activator). For example, the BAX activator can be a small molecule that activates BAX through interaction with the N-terminal activation site of BAX (such as BAX trigger site activator 1 (BTSA1); see Reyna et al., *Cancer Cell* 32:490-505, 2017).

B cell lymphoma 2 (Bcl-2): An anti-apoptotic member of the Bcl-2 family of proteins. Bcl-2 is an integral outer mitochondrial membrane protein. The human Bcl-2 protein is encoded by the BCL2 gene (see NCBI Gene ID 596).

B cell lymphoma extra-large (Bcl-xL): An anti-apoptotic member of the Bcl-2 family of proteins. Bcl-xL protein localizes to the outer mitochondrial membrane and plays a role in regulating mitochondrial membrane potential. The human Bcl-xL protein is encoded by the BCL2L1 gene (see NCBI Gene ID 598).

BAK: A pro-apoptotic member of the Bcl-2 family of proteins. BAK localizes to the mitochondria and contains BH1, BH2, BH3 and BH4 domains. The human BAK protein is encoded by the BAK1 gene (see NCBI Gene ID 578).

BAX: A pro-apoptotic member of the Bcl-2 family of proteins. BAX contains BH1, BH2, BH3 and BH4 domains. The human BAX protein is encoded by the BAX gene (see NCBI Gene ID 581).

Bcl-2 family: A family of proteins that contain at least one Bcl-2 homology (BH) domain and play a role in the apoptosis pathway. Members of this family have one or more types of BH domains referred to as BH1, BH2, BH3 and BH4. Anti-apoptotic members have at least BH1 and BH2 domains, while all pro-apoptotic members have at least a BH3 domain, which is necessary for dimerization with other Bcl-2 family proteins. Pro-apoptotic Bcl-2 family members include, but are not limited to, Bax, Bak, Bid, BIM, Bmf, Bad, Puma and Noxa; anti-apoptotic members include, for example, Bcl-2, Bcl-xL, Mcl-1, Bcl-w and A1 (see, for example, Shamas-Din et al., *Cold Spring Harb Perspect Biol* 5:a008714, 2013). As used herein, a "heterodimeric complex" of Bcl-2 family members refers to any complex of two Bcl-2 family member proteins where the two proteins are different from one another. Exemplary heterodimeric complexes include BIM-Bcl-2, BIM-Bcl-xL, BIM-Mcl-1 and BAX-BAK.

Bcl-2 homology 3 (BH3) mimetic: A small molecule that mimics the binding of BH3 peptides to the BH3 domain-binding groove of anti-apoptotic proteins. BH3 mimetics inhibit one or multiple members of the Bcl-2 protein family. Exemplary BH3 mimetics that can be used with the disclosed methods are listed in FIGS. 8A-8C and in the table below:

| Drug Name(s) | Inhibits |
|---|---|
| Venetoclax (ABT-199, VENCLEXTA ®, VENCLYXTO ®) | Bcl-2 |
| Novitoclax (ABT263, ABT737) | Bcl-2, Bcl-xL and Bcl-w |
| Obatoclax (GX15-070) | Bcl-2, Bcl-xL, Bcl-w and Mcl-1 |
| Gossypol (AT-101) | Bcl-2, Bcl-xL, Bcl-w and Mcl-1 |
| WEHI-539 | Bcl-xL |
| S63845 | Mcl-1 |
| MIK665 (S64315) | Mcl-1 |
| AMG176 | Mcl-1 |
| S1 | Bcl-2, Mcl-1 |
| ApoG2 | Bcl-2, Bcl-xL and Mcl-1 |
| BI-97D6 | Bcl-2, Bcl-xL and Mcl-1 |
| BIM SAHB | Bcl-W, Bcl-xL, Mcl-1, A1 |
| MIM 1 | Mcl-1 |

BIM: A pro-apoptotic member of the Bcl-2 family of proteins. BIM is referred to as a "BH3 protein" because it contains a BH3 domain, but not BH1, BH2 or BH4 domains. The human BIM protein is encoded by the BCL2L11 gene (see NCBI Gene ID 10018).

Binding affinity: Affinity of an antibody for an antigen. In one embodiment, affinity is calculated by a modification of the Scatchard method described by Frankel et al., Mol. Immunol., 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. In other embodiments, antibody affinity is measured by flow cytometry or by surface plasmon reference. An antibody that "specifically binds" an antigen (such as mesothelin) is an antibody that binds the antigen with high affinity and does not significantly bind other unrelated antigens.

In some examples, an antibody or fragment thereof (such as a BIM, Bcl-2, Bcl-xL, Mcl-1, BAX or BAK antibody) specifically binds to a target (such as a BIM, Bcl-2, Bcl-xL, Mcl-1, BAX or BAK) with a binding constant that is at least $10' M^{-1}$ greater, $10^4 M^{-1}$ greater or $105 M^{-1}$ greater than a binding constant for other molecules in a sample or subject. In some examples, an antibody (e.g., monoclonal antibody) or fragments thereof, has an equilibrium constant (Kd) of 1 nM or less. For example, an antibody or fragment thereof binds to a target, such as BIM, Bcl-2, Bcl-xL, Mcl-1, BAX or BAK, with a binding affinity of at least about $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M. In certain embodiments, a specific binding agent that binds to target has a dissociation constant (Kd) of ≤104 nM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-1}3$ M). In one embodiment, Kd is measured by a radiolabeled antigen binding assay (RIA) performed with the Fab version of an antibody of interest and its antigen (see, e.g., Chen et al., J. Mol. Biol. 293:865-881, 1999). In another example, Kd is measured using surface plasmon resonance assays using a BIACORES-2000 or a BIA-CORES-3000 (BIAcore, Inc., Piscataway, N.J.) at 25° C. with immobilized antigen CM5 chips at about 10 response units (RU).

Biological sample: A sample obtained from a subject (such as a human or veterinary subject), which can include cells. The biological sample can be a tissue sample or a biological fluid sample. In some examples, the biological sample includes a tissue sample, a biopsy sample, a fine-needle tumor aspirate, a bone marrow aspirate, or a blood sample. In one example the biological sample includes a tumor cell or cancer cell.

Conjugated: Refers to two molecules that are bonded together, for example by covalent bonds. An example of a conjugate is a molecule (such as avidin/streptavidin) conjugated to a detectable label, such as a fluorophore, to form a detection substrate. In one example, an detectable label is conjugated or attached to an antibody (such as one specific for BIM, Bcl-2, Bcl-xL, Mcl-1, BAX or BAK).

Contacting: Placement in direct physical association; includes both in solid and liquid form. As used herein, "contacting" is used interchangeably with "exposed."

Control: A reference standard, for example a positive control or negative control. A positive control is known to provide a positive test result. A negative control is known to provide a negative test result. However, the reference standard can be a theoretical or computed result, for example a result obtained in a population.

Cyclin-dependent kinase (CDK) inhibitor: A compound that inhibits the function of one or more CDKs. CDKs are a family of protein kinases involved in regulating the cell cycle. CDKs bind regulatory proteins called cyclins. It is the cyclin-CDK complexes that are kinase active; unbound CDK possesses very little kinase activity. CDK inhibitors function by interacting with CDK or cyclin-CDK complexes to disrupt kinase activity. Exemplary CDK inhibitors include, but are not limited to, from palbociclib (Ibrance™; PD-0332991), ribociclib (LEE011), abemaciclib (LY2835219), P1446A-05; Trilaciclib (G1T28), flavopiridol (alvocidib), olomoucine, and seliciclib (Roscovitine, CYC202).

Death receptor pathway inhibitor: Any agent or molecule that blocks or inhibits death receptor pathway signaling. In some examples, the death receptor pathway inhibitor is a death receptor agonist, such as an antibody that targets death receptor 4 (DR4) or DR5 (see, for example, Ukrainskaya et al., Acta Naturae 9(3):55-63, 2017).

Detectable label: A compound or composition that is conjugated (for example, covalently linked) directly or indirectly to another molecule (such as an antibody) to facilitate detection of that molecule. Specific non-limiting examples of labels include fluorescent and fluorogenic moieties (for example, fluorophores), chromogenic moieties, haptens (such as biotin, digoxigenin, and fluorescein), affinity tags, and radioactive isotopes (such as $^{32}P$, $^{33}P$, $^{35}S$, and $^{125}I$). The label can be directly detectable (such as optically detectable) or indirectly detectable (for example, via interaction with one or more additional molecules that are in turn detectable). Any method for labeling proteins, such as antibodies, can be used. In some examples, herein, the detectable label includes biotin, a peptide sequence tag, a fluorescent label, a luminescence label, an enzyme, a nucleotide sequence tag, a nanoparticle, or a combination thereof.

Drug targeting the apoptosis pathway: Any drug that modulates that apoptotic pathway. Examples include, but are not limited to, BH3 mimetics, direct BAX/BAK modulators, IAP inhibitors, CDK inhibitors, and death receptor pathway inhibitors.

Effective amount (or therapeutically effective amount): The amount of an agent (such as a drug targeting the apoptosis pathway, such as BH3 mimetic, a BAX/BAK modulator, an inhibitor of apoptosis protein (IAP) inhibitor, a CDK inhibitor, or a death receptor pathway inhibitor, as well as other anti-cancer agents) that is sufficient to effect beneficial or desired results. An effective amount (also referred to as a therapeutically effective amount) may vary depending upon one or more of: the subject and disease condition being treated, the weight and age of the subject, the severity of the disease condition, the manner of administration and the like. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition. In one embodiment, an "effective amount" (e.g., of a drug targeting the apoptosis pathway, or other anti-cancer drug) is an amount sufficient to reduce the volume/size of a tumor, the weight of a tumor, the number of metastases, reduce the volume/size of a metastasis, the weight of a metastasis, or combinations thereof, for example by at least 10%, at least 20%, at least 25%, at least 50%, at least 70%, at least 75%, at least 80%, at least 90%, at least 95%, or at least 99% (as compared to no administration of the therapeutic agent). In one embodiment, an "effective amount" (e.g., of a drug targeting the apoptosis pathway, or other anti-cancer drug) is an amount sufficient to increase T cell infiltration, for example into a tumor or tumor microenvironment, by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the therapeutic agent).

Epitope: An antigenic determinant. Epitopes are particular chemical groups or contiguous or non-contiguous peptide sequences on a molecule that are antigenic, that is, that elicit a specific immune response. An antibody binds a particular antigenic epitope based on the three dimensional structure of the antibody and the matching (or cognate) epitope.

Fluorescent protein: A protein that emits light of a certain wavelength when exposed to a particular wavelength of light. Fluorescent proteins include, but are not limited to, green fluorescent proteins, blue fluorescent proteins, cyan fluorescent proteins, yellow fluorescent proteins, orange fluorescent proteins, red fluorescent proteins and modified versions thereof.

Fluorophore: A chemical compound, which when excited by exposure to a particular wavelength of light, emits light (i.e., fluoresces), for example at a different wavelength than that to which it was exposed. Also encompassed by the term "fluorophore" are luminescent molecules, which are chemical compounds which do not require exposure to a particular wavelength of light to fluoresce; luminescent compounds naturally fluoresce. Therefore, the use of luminescent signals eliminates the need for an external source of electromagnetic radiation, such as a laser. An example of a luminescent molecule includes, but is not limited to, aequorin (Tsien, 1998, Ann. Rev. Biochem. 67:509).

Exemplary fluorophores include, but are not limited to, 6-carboxyfluorescein (FAM), tetrachlorofluorescein (TET), tetramethylrhodamine (TMR), hexachlorofluorescein (HEX), JOE, ROX, CAL Fluor™, Pulsar™, Quasar™, Texas Red™, Cy™3 and Cy™5. Other examples of fluorophores are provided in U.S. Pat. No. 5,866,366. These include: 4-acetamido-4'-isothiocyanatostilbene-2,2'disulfonic acid, acridine and derivatives such as acridine and acridine isothiocyanate, 5-(2'-aminoethyl)amino-naphthalene-1-sulfonic acid (EDANS), 4-amino-N-[3-vinylsulfonyl)phenyl]-naphthalimide-3,5 disulfonate (Lucifer Yellow VS), N-(4-anilino-1-naphthyl)-maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethyl-amino] naphthalene-1-sulfonyl chloride (DNS, dansyl chloride); 4-(4'-dimethyl-aminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other fluorophores include thiol-reactive europium chelates that emit at approximately 617 nm (Heyduk and Heyduk, Analyt. Biochem. 248:216-27, 1997; J. Biol. Chem. 274:3315-22, 1999).

Other fluorophores include cyanine, merocyanine, stryl, and oxonyl compounds, such as those disclosed in U.S. Pat. Nos. 5,627,027; 5,486,616; 5,569,587; and 5,569,766, and in published PCT application no. US98/00475, each of which is incorporated herein by reference. Specific examples of fluorophores disclosed in one or more of these patent documents include Cy3 and Cy5, for instance, and substituted versions of these fluorophores.

Other fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al., herein incorporated by reference) and derivatives thereof. Other fluorophores are available, such as from Molecular Probes/Life Technologies.

Fusion protein: A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Heterologous: A heterologous protein or polypeptide refers to a protein or polypeptide derived from a different source or species.

Inhibitor of apoptosis protein (IAP) inhibitor: An agent that inhibits the IAP family. In some examples herein, the IAP inhibitor is a second mitochondrial activator of caspases (SMAC) mimetic, such as AT-406/Debio-1143, GDC-0917/CUDC-427, LCL-161, GDC-0152, Birinapant, HGS1029/AEG40826/ASTX-660 (see Bai et al., Pharmacol Ther 144: 82-95, 2014).

Isolated: An "isolated" biological component (such as a nucleic acid molecule, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Linker: One or more nucleotides or amino acids that serve as a spacer between two molecules, such as between two nucleic acid molecules or two peptides (such as in a fusion protein).

Mcl-1: An anti-apoptotic member of the Bcl-2 family of proteins. Mcl-1 contains all four BH domains. The human Mcl-1 protein is encoded by the MCL1 gene (see NCBI Gene ID 4170).

Solid support: Any solid material to which a molecule, such as a protein (for example, an antibody) can be bound, either directly or via a linker. Examples of solid supports include, but are not limited to, beads (such as those composed of glass, metal, or plastic), tissue culture plates (such as a multi-well plate) and affinity matrices (such as an affinity column).

Subject: Living multi-cellular vertebrate organisms, a category that includes human and non-human mammals.

Synthetic: Produced by artificial means in a laboratory, for example a synthetic nucleic acid can be chemically synthesized in a laboratory.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests (such as imaging), and the like. In some examples, treatment with the disclosed methods results in a decrease in the number, volume, and/or weight of a tumor and/or metastases.

Tumor, neoplasia, malignancy or cancer: A neoplasm is an abnormal growth of tissue or cells which results from excessive cell division. Neoplastic growth can produce a tumor. The amount of a tumor in an individual is the "tumor burden" which can be measured as the number, volume, and/or weight of the tumor. A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Exemplary tumors, such as cancers, that can be analyzed and/or treated using the disclosed methods include solid tumors, such as breast carcinomas (e.g. lobular and duct carcinomas, such as a triple negative breast cancer), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, head and neck squamous cell carcinoma, and lymphatic tumors (including B-cell and T-cell malignant lymphoma).. In one example, the tumor is an adenocarcinoma.

The disclosed methods can also be used to treat and evaluate liquid tumors, such as a lymphatic, white blood cell, or other type of leukemia. In a specific example, the tumor treated is a tumor of the blood, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), a lymphoma (such as Hodgkin's lymphoma or non-Hodgkin's lymphoma), or a myeloma.

III. Overview of Several Embodiments

Figure 5A:
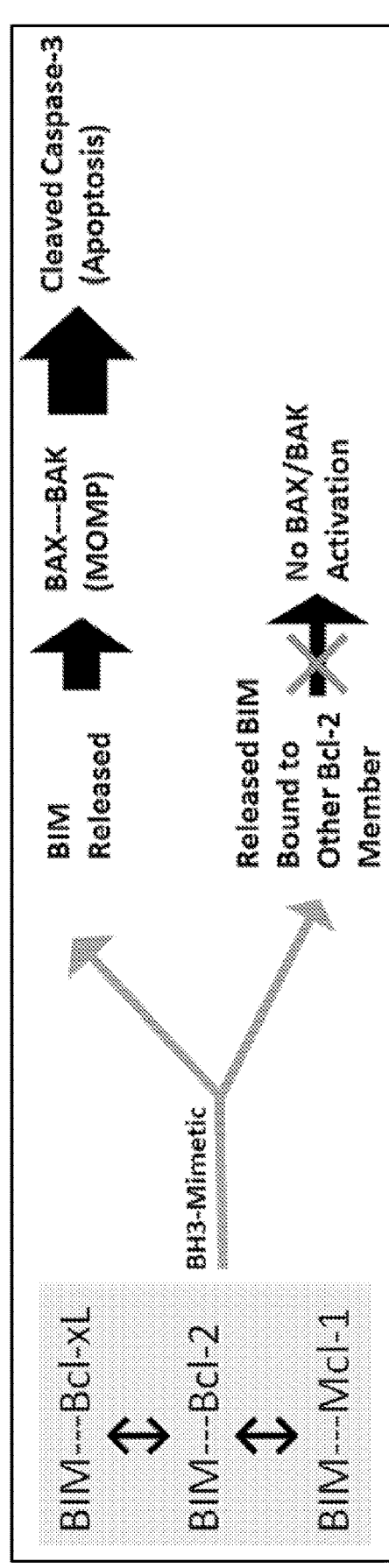
FIGS. 5A-5E include a schematic and graphs showing heterodimer levels in untreated and BH3 mimetic treated AMO-1 and Mv4-11 cells.

The present disclosure describes the development and use of heterodimer immunoassays to detect Bcl-2 family heterodimers containing BIM (BIM-Bcl-2, BIM-Bcl-xL and BIM-Mcl-1 heterodimers) or BAX (BAX-BAK heterodimers), such as for determining the sensitivity of a cancer to a BH3 mimetic or other drug targeting the apoptosis pathway. BIM is a pro-apoptotic member of the Bcl-2 protein family that heterodimerizes with several anti-apoptotic family members, including Bcl-2, Bcl-xL and Mcl-1. When a BH3 mimetic (or other agent) disrupts BIM-containing heterodimeric complexes, BIM is free to promote apoptosis (see FIG. 5A). Thus, a drug targeting the apoptosis pathway (such as a BH3 mimetic) that is capable of disrupting BIM-containing heterodimers in cancer cells is a good candidate for treatment of that cancer. Both BAX and BAK are pro-apoptotic members of the Bcl-2 family. Therefore, an increase in BAX and BAK heterodimers in cancer cells following treatment with a drug (e.g., by administering the drug in a therapeutically effective amount to the subject) indicates the drug will be effective for treating the cancer by promoting apoptosis of the cancer cells.

Levels of Bcl-2 family heterodimer complexes can be measured in tumor tissue biopsies (including fine needle aspirates), cancer cells, plasma cells from blood or bone marrow, or any surrogate tissues. This disclosure is in part based on the discovery that a Mcl-1 inhibitor is more effective in cell lines that have higher levels of BIM-Mcl-1 heterodimer proteins in cell lysates, as determined by a sandwich immunoassay described herein. To select an appropriate drug targeting the apoptosis pathway (such as a BH3 mimetic, such as one shown in the Tables above) for treating a particular type of cancer, the disclosed methods can be used to evaluate the level of BIM-containing heterodimeric complexes. For example, a high level of BIM-Bcl-xL heterodimers in the cancer cells indicates that a BH3 mimetic that functions as a Bcl-xL inhibitor would be effective for treating the cancer. Similarly, a high level of BIM-Mcl-1 heterodimers in the cancer cells indicates that a BH3 mimetic that functions as an Mcl-1 inhibitor would be effective for treating the cancer.

The data disclosed herein demonstrate the applicability of the heterodimer assays, such as for testing and confirming the precise mechanism of drug resistance in different cancer patients; identifying patients who will benefit from a given BH3 mimetic treatment alone or in a combination with another drug; providing pharmacodynamic measurements of a BH3 inhibitor to demonstrate target engagement and provide evidence of the mechanism-of-action; and directly comparing the potency of multiple BH3 mimetics to identify the best in class agent.

Provided herein is a method of detecting a Bcl-2 family heterodimeric complex in a biological sample. In some embodiments, the method includes providing a cell lysate generated from a biological sample containing cells (such as cancer cells). The method includes detecting the presence of a heterodimeric Bcl-2 family protein complex in the cell lysate, wherein the heterodimeric complex comprises a first protein and a second protein, and wherein the heterodimeric complex is selected from the group consisting of BIM-Bcl-2, BIM-Bcl-xL, BIM-Mcl-1 and BAX-BAK. In some examples, detecting the heterodimeric complex includes providing an antibody specific for the first protein bound to a solid support; providing a detection antibody specific for the second protein; contacting the cell lysate with the antibody-bound solid support and the detection antibody; and detecting the presence of the detection antibody. The cell lysate analyzed includes proteins. In some examples, the cell lysate includes a nuclear and/or mitochondrial fraction. In other examples, the cell lysate includes a cytosolic fraction. In specific examples, the cell lysate includes a nuclear/mitochondrial fraction and a cytosolic fraction.

In some embodiments, the biological sample includes a tissue sample, a biopsy sample, a fine-needle tumor aspirate, a bone marrow aspirate or a blood sample (or a fraction thereof, such as plasma or serum).

In some embodiments, the solid support comprises a bead, such as a glass bead, a plastic bead or a magnetic bead. In specific examples, the solid support is a Luminex bead.

In other embodiments, the solid support includes a tissue culture plate or an affinity matrix.

In some embodiments, the detection antibody includes a detectable label, for example is covalently attached to the detectable label. In some examples, the detectable label comprises biotin, a peptide sequence tag, a fluorescent label, a luminescence label, an enzyme, a nucleotide sequence tag, a nanoparticle, or a combination thereof.

In some embodiments, the method is a multiplex detection method that comprises or consists of detecting two different heterodimeric complexes selected from the group consisting of BIM-Bcl-2, BIM-Bcl-xL, BIM-Mcl-1 and BAX-BAK. In some examples, the method comprises or consists of detecting BIM-Bcl-2 and BIM-Bcl-xL; BIM-Bcl-2 and BIM-Mcl-1; BIM-Bcl-2 and BAK-BAK; BIM-Bcl-xL and BIM-Mcl-1; BIM-Bcl-xL and BAK-BAK; or BIM-Mcl-1 and BAX-BAK.

In some embodiments, the method is a multiplex detection method that comprises or consists of detecting three different heterodimeric complexes selected from the group consisting of BIM-Bcl-2, BIM-Bcl-xL, BIM-Mcl-1 and BAX-BAK. In some examples, the method comprises or consists of detecting BIM-Bcl-2, BIM-Bcl-xL and BIM-Mcl-1; BIM-Bcl-2, BIM-Bcl-xL and BAX-BAK; BIM-Bcl-xL, BIM-Mcl-1 and BAX-BAK; BIM-Bcl-2, BIM-Mcl-1 and BAX-BAK; or BIM-Bcl-2, BIM-Bcl-xL and BAX-BAK.

In some embodiments, the method is a multiplex detection method that comprises or consists of detecting all four different heterodimeric complexes (BIM-Bcl-2, BIM-Bcl-xL, BIM-Mcl-1 and BAX-BAK).

In some embodiments, the method further includes determining the concentration (e.g., qualitative or quantitative) of the heterodimeric complex in the cell lysate by comparing the amount of the heterodimeric complex in the cell lysate with the amount of total protein present in the cell lysate.

In some embodiments, the biological sample is from a subject diagnosed with cancer (such as a breast cancer, prostate cancer, ovarian cancer, uterine cancer, pancreatic cancer, hepatocellular carcinoma, colorectal cancer, lung cancer, kidney cancer, head-and-neck cancer, AML, CLL, or melanoma), and the method further includes treating the subject with a drug targeting the apoptosis pathway. In some examples, the drug targeting the apoptosis pathway is selected from the group consisting of a BH3 mimetic, a BAX/BAK modulator, an inhibitor of apoptosis protein (IAP) inhibitor, a CDK inhibitor, and a death receptor pathway inhibitor. In specific non-limiting examples, the BH3 mimetic is an inhibitor of Mcl-1, such as S63845, MIK665 or AMG176. In other specific non-limiting examples, the BH3 mimetic is an inhibitor of Bcl-2 (such as venetoclax), an inhibitor of Bcl-xL (such as WEHI-539), or an inhibitor of both Bcl-2 and Bcl-xL (such as novitoclax, obatoclax or gossypol).

Also provided herein is a method of selecting a subject diagnosed with cancer (such as a breast cancer, prostate cancer, ovarian cancer, uterine cancer, pancreatic cancer, hepatocellular carcinoma, colorectal cancer, lung cancer, kidney cancer, head-and-neck cancer, AML, CLL, or melanoma) as suitable for treatment with a drug targeting the apoptosis pathway. In some embodiments, the method includes providing a biological sample obtained from the subject, wherein the biological sample includes cancer cells; culturing the cells of the biological sample in the presence and absence of the drug; preparing a cell lysate from the cells cultured in the presence of the drug and a cell lysate from the cells cultured in the absence of the drug; and detecting Bcl-2 family heterodimeric complexes in each cell lysate, wherein the heterodimeric complexes comprise a first protein and a second protein, and wherein the heterodimeric complexes are selected from the group consisting of BIM-Bcl-2, BIM-Bcl-xL, BIM-Mcl-1 and BAX-BAK. In an alternative embodiment, a cell lysate is prepared from the biological sample and the drug is added to the cell lysate. In this alternative embodiment, the method includes providing a biological sample obtained from the subject, wherein the biological sample comprises cancer cells; preparing a cell lysate from the cells of the biological sample; and detecting Bcl-2 family heterodimeric complexes in the cell lysate in the presence and absence of the drug, wherein the heterodimeric complexes comprise a first protein and a second protein, and wherein the heterodimeric complexes are selected from the group consisting of BIM-Bcl-2, BIM-Bcl-xL, BIM-Mcl-1 and BAX-BAK. In some examples, detecting the Bcl-2 family heterodimeric complexes includes providing an antibody specific for the first protein bound to a solid support; providing a detection antibody specific for the second protein; contacting the cell lysates with the antibody-bound solid support and the detection antibody; and detecting the presence of the detection antibody. A decrease in BIM-Bcl-2, BIM-Bcl-xL and/or BIM-Mcl-1 heterodimeric complexes, or an increase in BAX-BAK heterodimeric complexes, in the presence of the drug compared to in the absence of the drug indicates the subject is suitable for treatment with the drug. In some examples, the decrease or increase in heterodimeric complexes is an increase or decrease of at least 5%, at least 10%, at least 20%, at least 30%, at least 40%, at least 50%, at least 60%, at least 70%, at least 80%, at least 90%, at least 100%, at least 150%, at least 200%, or at least 250%.

The cell lysate can include proteins. In some examples, the cell lysate includes a nuclear and/or mitochondrial fraction. In other examples, the cell lysate includes a cytosolic fraction. In specific examples, the cell lysate includes a nuclear/mitochondrial fraction and a cytosolic fraction.

In some embodiments, the biological sample includes a tissue sample, a biopsy sample, a tumor aspirate, a bone marrow aspirate or a blood sample (or a fraction thereof, such as blood or serum).

In some embodiments, the solid support includes a bead, such as a glass bead, a plastic bead or a magnetic bead. In specific examples, the solid support is a Luminex bead.

In other embodiments, the solid support includes a tissue culture plate or an affinity matrix.

In some embodiments, the detection antibody includes a detectable label. In some examples, the detectable label comprises biotin, a peptide sequence tag, a fluorescent label, a luminescence label, an enzyme, a nucleotide sequence tag, a nanoparticle, or a combination thereof.

In some embodiments, the method is a multiplex detection method that comprises or consists of detecting two different heterodimeric complexes selected from the group consisting of BIM-Bcl-2, BIM-Bcl-xL, BIM-Mcl-1 and BAX-BAK. In some examples, the method comprises or consists of detecting BIM-Bcl-2 and BIM-Bcl-xL; BIM-Bcl-2 and BIM-Mcl-1; BIM-Bcl-2 and BAK-BAK; BIM-Bcl-xL and BIM-Mcl-1; BIM-Bcl-xL and BAK-BAK; or BIM-Mcl-1 and BAX-BAK.

In some embodiments, the method is a multiplex detection method that comprises or consists of detecting three different heterodimeric complexes selected from the group consisting of BIM-Bcl-2, BIM-Bcl-xL, BIM-Mcl-1 and BAX-BAK. In some examples, the method comprises or consists of detecting BIM-Bcl-2, BIM-Bcl-xL and BIM-Mcl-1; BIM-Bcl-2, BIM-Bcl-xL and BAX-BAK; BIM-Bcl-xL, BIM-Mcl-1 and BAX-BAK; BIM-Bcl-2, BIM-Mcl-1 and BAX-BAK; or BIM-Bcl-2, BIM-Bcl-xL and BAX-BAK.

In some embodiments, the method is a multiplex detection method that comprises or consists of detecting all four different heterodimeric complexes (BIM-Bcl-2, BIM-Bcl-xL, BIM-Mcl-1 and BAX-BAK).

In some embodiments, the cancer is a solid tumor. In other embodiments, the cancer is a hematopoietic cancer.

In some embodiments, the method further includes treating the subject with the drug targeting the apoptosis pathway. In some examples, the drug targeting the apoptosis pathway is selected from the group consisting of a BH3 mimetic, a BAX/BAK modulator, an IAP inhibitor, a CDK inhibitor, and a death receptor pathway inhibitor. In specific non-limiting examples, the BH3 mimetic is an inhibitor of Mcl-1, such as S63845, MIK665 or AMG176. In other specific non-limiting examples, the BH3 mimetic is an inhibitor of Bcl-2 (such as venetoclax), an inhibitor of Bcl-xL (such as WEHI-539), or an inhibitor of both Bcl-2 and Bcl-xL (such as novitoclax, obatoclax or gossypol).

Further provided herein is a method for selecting a drug targeting the apoptosis pathway that is effective for treating cancer (such as a breast cancer, prostate cancer, ovarian cancer, uterine cancer, pancreatic cancer, hepatocellular carcinoma, colorectal cancer, lung cancer, kidney cancer, head-and-neck cancer, AML, CLL, or melanoma) in a subject. In some embodiments, the method includes providing a biological sample obtained from the subject, wherein the biological sample includes cancer cells; culturing the cells of the biological sample in the presence and absence of a candidate drug targeting the apoptosis pathway; preparing a cell lysate from the cells cultured in the presence of the candidate drug and a cell lysate from the cells cultured in the absence of the candidate drug; and detecting Bcl-2 family heterodimeric complexes in each cell lysate, wherein the heterodimeric complexes comprise a first protein and a second protein, and wherein the heterodimeric complexes are selected from the group consisting of BIM-Bcl-2, BIM-Bcl-xL, BIM-Mcl-1 and BAX-BAK. In an alternative embodiment, a cell lysate is prepared from the biological sample and the candidate drug is contacted with the cell lysate. In this alternative embodiment, the method includes providing a biological sample obtained from the subject, wherein the biological sample comprises cancer cells; preparing a cell lysate from the cancer cells of the biological sample; and detecting Bcl-2 family heterodimeric complexes in the cell lysate in the presence and absence of a candidate drug targeting the apoptosis pathway, wherein the heterodimeric complexes comprise a first protein and a second protein, and wherein the heterodimeric complexes are selected from the group consisting of BIM-Bcl-2, BIM-Bcl-xL, BIM-Mcl-1 and BAX-BAK. In some examples, detecting the Bcl-2 family heterodimeric complexes includes providing an antibody specific for the first protein bound to a solid support; providing a detection antibody specific for the second protein; contacting the cell lysates with the antibody-bound solid support and the detection antibody; and detecting the presence of the detection antibody. A decrease in BIM-Bcl-2, BIM-Bcl-xL and/or BIM-Mcl-1 heterodimeric complexes, or an increase in BAX-BAK heterodimeric complexes, in the presence of the candidate drug targeting the apoptosis pathway compared to in the absence of the candidate drug indicates the candidate drug targeting the apoptosis pathway is effective for treating the cancer. In some examples, the decrease or increase in heterodimeric complexes is an increase or decrease of at least 5%, at least 10%, at least 20%, at least 30%, at least 40%, at least 50%, at least 60%, at least 70%, at least 80%, at least 90%, at least 100%, at least 150%, at least 200%, or at least 250%.

The cell lysate can include proteins. In some examples, the cell lysate includes a nuclear and/or mitochondrial fraction. In other examples, the cell lysate includes a cytosolic fraction. In specific examples, the cell lysate includes a nuclear/mitochondrial fraction and a cytosolic fraction.

In some embodiments, the biological sample includes a tissue sample, a biopsy sample, a tumor aspirate, a bone marrow aspirate or a blood sample (or a fraction thereof, such as blood or serum).

In some embodiments, the solid support includes a bead, such as a glass bead, a plastic bead or a magnetic bead. In specific examples, the solid support is a Luminex bead.

In other embodiments, the solid support includes a tissue culture plate or an affinity matrix.

In some embodiments, the detection antibody includes a detectable label. In some examples, the detectable label comprises biotin, a peptide sequence tag, a fluorescent label, a luminescence label, an enzyme, a nucleotide sequence tag, a nanoparticle, or a combination thereof.

In some embodiments, the method is a multiplex detection method that comprises or consists of detecting two different heterodimeric complexes selected from the group consisting of BIM-Bcl-2, BIM-Bcl-xL, BIM-Mcl-1 and BAX-BAK. In some examples, the method comprises or consists of detecting BIM-Bcl-2 and BIM-Bcl-xL; BIM-Bcl-2 and BIM-Mcl-1; BIM-Bcl-2 and BAK-BAK; BIM-Bcl-xL and BIM-Mcl-1; BIM-Bcl-xL and BAK-BAK; or BIM-Mcl-1 and BAX-BAK.

In some embodiments, the method is a multiplex detection method that comprises or consists of detecting three different heterodimeric complexes selected from the group consisting of BIM-Bcl-2, BIM-Bcl-xL, BIM-Mcl-1 and BAX-BAK. In some examples, the method comprises or consists of detecting BIM-Bcl-2, BIM-Bcl-xL and BIM-Mcl-1; BIM-Bcl-2, BIM-Bcl-xL and BAX-BAK; BIM-Bcl-xL, BIM-Mcl-1 and BAX-BAK; BIM-Bcl-2, BIM-Mcl-1 and BAX-BAK; or BIM-Bcl-2, BIM-Bcl-xL and BAX-BAK.

In some embodiments, the method is a multiplex detection method that comprises or consists of detecting all four different heterodimeric complexes (BIM-Bcl-2, BIM-Bcl-xL, BIM-Mcl-1 and BAX-BAK).

In some embodiments, the cancer is a solid tumor. In other embodiments, the cancer is a hematopoietic cancer.

In some embodiments, the method further includes treating the subject with the drug targeting the apoptosis pathway. In some examples, the drug targeting the apoptosis pathway is selected from the group consisting of a BH3 mimetic, a BAX/BAK modulator, an IAP inhibitor, a CDK inhibitor, and a death receptor pathway inhibitor. In specific non-limiting examples, the BH3 mimetic is an inhibitor of Mcl-1, such as S63845, MIK665 or AMG176. In other specific non-limiting examples, the BH3 mimetic is an inhibitor of Bcl2 (such as venetoclax), an inhibitor of Bcl-xL (such as WEHI-539), or an inhibitor of both Bcl-2 and Bcl-xL (such as novitoclax, obatoclax or gossypol).

IV. Treatment

As discussed above, in some examples, the method includes treating the subject with a drug targeting the apoptosis pathway. For example, if a decrease in BIM-Bcl-2, BIM-Bcl-xL and/or BIM-Mcl-1 heterodimeric complexes, or an increase in BAX-BAK heterodimeric complexes, is measured in the sample obtained from the subject (such as a cell lysate prepared from such a sample) the subject has a cancer suitable for treatment with the drug. Thus, the methods can include administering an effective amount of one or more drugs targeting the apoptosis pathway, such as a BH3 mimetic, a BAX/BAK modulator, an IAP inhibitor, a CDK inhibitor, or a death receptor pathway inhibitor. Specific examples of such drugs are provided herein. In one example, venetoclax, novitoclax, obatoclax, or gossypol is administered in an effective amount. In one example, novitoclax is administered in an effective amount. In one example, WEHI-539, S63845, MIK665 (S64315), or AMG176 is administered in an effective amount. In one example, S1, ApoG2, BI-97D6, BIM SAHB, MIM 1 is administered in an effective amount. In one example, S63845 is administered in an effective amount.

The subject treated with the drug targeting the apoptosis pathway can receive one or more additional therapies, such as one or more of an effective amount of chemotherapy, an effective amount of radiotherapy (for example administration of radioactive material or energy (such as external beam therapy) to the tumor site to help eradicate the tumor or shrink it), an effective amount of a biologic (such as a therapeutic monoclonal antibody), and surgery (for example surgical resection of the cancer or a portion of it).

In one example, the subject is further treated with one or more chemotherapeutic agents. Chemotherapeutic agents include any chemical agent with therapeutic usefulness in the treatment of diseases characterized by abnormal cell growth, such as cancer. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology 2$^{nd}$ ed., © 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Willians & Wilkins, 2005; Skeel, *Handbook of Cancer Chemotherapy* (6th ed.). Lippincott Williams & Wilkins, 2003). Combination chemotherapy is the administration of more than one agent to treat cancer.

Examples of chemotherapeutic agents that can be used include alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Specific non-limiting examples of alkylating agents are temozolomide and dacarbazine. Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone).

Examples of commonly used chemotherapy drugs include Adriamycin, Alkeran, Ara-C, BiCNU, Busulfan, CCNU, Carboplatinum, Cisplatinum, Cytoxan, Daunorubicin, DTIC, 5-fluorouracil (5-FU), Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Additional therapeutic agents that can be used include microtubule binding agents, DNA intercalators or crosslinkers, DNA synthesis inhibitors, DNA and/or RNA transcription inhibitors, antibodies, enzymes, enzyme inhibitors, gene regulators, angiogenesis inhibitors. These agents (which are administered at a therapeutically effective amount) and treatments can be used alone or in combination. Methods and therapeutic dosages of such agents are known and can be determined by a skilled clinician.

"Microtubule binding agents" refers to agents that interact with tubulin to stabilize or destabilize microtubule formation thereby inhibiting cell division. Examples of microtubule binding agents that can be used in conjunction with the disclosed therapies include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

Suitable DNA and/or RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-fluorouracil (5-FU) and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof.

The disclosed methods can further include administering to the subject a therapeutically effective amount of an immunotherapy. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor;

Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech). The immunotherapeutic agent can be a PD-1 antagonist or a PD-L1 antagonist, such as an antibody (such as a monoclonal antibody) that specifically binds PD-1 or PD-L1, such as Atezolizumab, MPDL3280A, BNS-936558 (Nivolumab), Pembrolizumab, Pidilizumab, CTO11, AMP-224, AMP-514, MEDI-0680, BMS-936559, BMS935559, MEDI-4736, MPDL-3280A, MSB-0010718C. The immunotherapeutic agent can also be a CTLA-4, LAG-3, or B7-H3 antagonist, such as Tremelimumab, BMS-986016, and MGA271.

Non-limiting examples of anti-angiogenic agents include molecules, such as proteins, enzymes, polysaccharides, oligonucleotides, DNA, RNA, and recombinant vectors, and small molecules that function to reduce or even inhibit blood vessel growth. Examples of suitable angiogenesis inhibitors include, without limitation, angiostatin KI-3, staurosporine, genistein, fumagillin, medroxyprogesterone, suramin, interferon-alpha, metalloproteinase inhibitors, platelet factor 4, somatostatin, thrombospondin, endostatin, thalidomide, and derivatives and analogs thereof. For example, in some embodiments the anti-angiogenesis agent is an antibody that specifically binds to VEGF (e.g., Avastin, Roche) or a VEGF receptor (e.g., a VEGFR2 antibody). In one example the anti-angiogenic agent includes a VEGFR2 antibody, or DMXAA (also known as Vadimezan or ASA404; available commercially, e.g., from Sigma Corp., St. Louis, MO) or both. The anti-angiogenic agent can be bevacizumab, sunitinib, an anti-angiogenic tyrosine kinase inhibitors (TKI), such as sunitinib, xitinib and dasatinib. These can be used individually or in any combination.

Exemplary kinase inhibitors include Gleevac, Iressa, and Tarceva, sunitinib, sorafenib, anitinib, and dasatinib that prevent phosphorylation and activation of growth factors. Antibodies that can be used include Herceptin and Avastin that block growth factors and the angiogenic pathway. These can be used individually or in combination.

In some examples, the additional therapeutic agent administered is a biologic, such as a monoclonal antibody, for example, 3F8, Abagovomab, Adecatumumab, Afutuzumab, Alacizumab, Alemtuzumab, Altumomab pentetate, Anatumomab mafenatox, Apolizumab, Arcitumomab, Bavituximab, Bectumomab, Belimumab, Besilesomab, Bevacizumab, Bivatuzumab mertansine, Blinatumomab, Brentuximab vedotin, Cantuzumab mertansine, Capromab pendetide, Catumaxomab, CC49, Cetuximab, Citatuzumab bogatox, Cixutumumab, Clivatuzumab tetraxetan, Conatumumab, Dacetuzumab, Detumomab, Ecromeximab, Eculizumab, Edrecolomab, Epratuzumab, Ertumaxomab, Etaracizumab, Farletuzumab, Figitumumab, Galiximab, Gemtuzumab ozogamicin, Girentuximab, Glembatumumab vedotin, Ibritumomab tiuxetan, Igovomab, Imciromab, Intetumumab, Inotuzumab ozogamicin, Ipilimumab, Iratumumab, Labetuzumab, Lexatumumab, Lintuzumab, Lorvotuzumab mertansine, Lucatumumab, Lumiliximab, Mapatumumab, Matuzumab, Mepolizumab, Metelimumab, Milatuzumab, Mitumomab, Morolimumab, Nacolomab tafenatox, Naptumomab estafenatox, Necitumumab, Nimotuzumab, Nofetumomab merpentan, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Satumomab pendetide, Sibrotuzumab, Sonepcizumab, Tacatuzumab tetraxetan, Taplitumomab paptox, Tenatumomab, TGN1412, Ticilimumab (tremelimumab), Tigatuzumab, TNX-650, Trastuzumab, Tremelim-umab, Tucotuzumab celmoleukin, Veltuzumab, Volociximab, Votumumab, Zalutumumab, or combinations thereof. In some examples, the therapeutic antibody is specific for PD-1 or PDL-1 (e.g., pembrolizumab and nivolumab). In some examples, the therapeutic antibody is specific for EGFR (e.g., cetuximab). In some examples, the therapeutic antibody is specific for VEGF (e.g., bevaci-zumab). In some examples, the subject is administered an effective amount of nonmyeloablative chemotherapy or radiotherapy. For example, the subject may receive an effective amount of nonmyeloablative chemotherapy, such as administration of one or more of cisplatin, fludarabine, idarubicin, melphalan, ara-C, 2-chlorodeoxyadenosine, anti-thymocyte globulin, and cyclophosphamide (such as 10 to 50 mg/kg body weight). In some examples, the subject receives an effective amount of solid tumor irradiation, thymic irradiation, or total body irradiation (e.g., 2 Gy), or combinations thereof.

V. Clinical Response

The disclosed methods can treat the tumor in the subject by reducing the volume or weight of the tumor, reducing the number of metastases, reducing the size or weight of a metastasis, or combinations thereof. In some examples a metastasis is cutaneous or subcutaneous. Thus, in some examples, administration of a drug targeting the apoptosis pathway treats a tumor in a subject by reducing the size or volume of the tumor by at least 10%, at least 20%, at least 30%, at least 40%, at least 50%, at least 60%, at least 70%, at least 75%, at least 80%, at least 90%, at least 95%, at least 98% or at least 99%, for example as compared to no administration of a drug targeting the apoptosis pathway. In some examples, administration of a drug targeting the apop-tosis pathway treats a tumor in a subject by reducing the weight of the tumor by at least 10%, at least 20%, at least 30%, at least 40%, at least 50%, at least 60%, at least 70%, at least 75%, at least 80%, at least 90%, at least 95%, at least 98% or at least 99%, for example as compared to no administration of a drug targeting the apoptosis pathway. In some examples, administration of a drug targeting the apop-tosis pathway treats a tumor in a subject by reducing the size or volume of a metastasis by at least 10%, at least 20%, at least 30%, at least 40%, at least 50%, at least 60%, at least 70%, at least 75%, at least 80%, at least 90%, at least 95%, at least 98% or at least 99%, for example as compared to no administration of a drug targeting the apoptosis pathway. In some examples, administration of a drug targeting the apop-tosis pathway treats a tumor in a subject by reducing the number of metastases by at least 10%, at least 20%, at least 30%, at least 40%, at least 50%, at least 60%, at least 70%, at least 75%, at least 80%, at least 90%, at least 95%, at least 98% or at least 99% for example as compared to no administration of a disclosed recombinant oncolytic virus or administration of a drug targeting the apoptosis pathway. In some examples, combinations of these effects are achieved.

The following examples are provided to illustrate certain particular features and/or embodiments. These examples should not be construed to limit the disclosure to the particular features or embodiments described.

EXAMPLES

Example 1: Antibodies and Calibrator Fusion Proteins

Antibodies specific for BIM, Bcl-2, Bcl-xL, Mcl-1, BAX and BAK were purchased from Trevigen, R&D Systems, Cell Signaling Technologies, Abcam, and ThermoFisher. Antibody preparations free from carrier proteins and stabi-lizers were conjugated to biotin using Sulfo-NHS-LC-Biotin (Thermo Scientific, Pierce EZ-Link) according to the manu-facturer's recommended procedures using a 25:1 biotin:antibody ratio.

Recombinant calibrator fusion proteins (BIM-Mcl-1, BIM-Bcl-2, BIM-Bcl-xL, and BAX-BAK) were designed at the Protein Expression Library (Leidos Biomedical Research, Inc., Frederick National Laboratory for Cancer Research).

Heterodimer fusion proteins included a 20-amino acid linker (GSGAGGSAGGSGAGSGAGSG; SEQ ID NO: 5) separating the two proteins of the heterodimer.

Amino acid sequences of the linked heterodimers are set forth herein as SEQ ID NO: 1 (BIM-Bcl-2), SEQ ID NO: 2 (BIM-Bcl-xL), SEQ ID NO: 3 (BIM-Mcl-1) and SEQ ID NO: 4 (BAX-BAK). Protein calibrator concentrations were based on BCA protein measurements.

Example 2: Preparation of Fine-Needle Tumor Aspirate Samples

This example describes a protocol for preparing frozen needle tumor biopsy samples for use in heterodimer immu-noassays. This method results in a cytosolic lysate fraction and a nuclear/mitochondrial lysate fraction.

Immediately after collection, tumor samples (~18 grams) are frozen in 1.5 mL conical bottomed tubes. To process a collected sample, the tube is moved to wet ice and 350 µL of pre-chilled mitochondrial isolation medium (MIM; 0.5 M EDTA, HEPES, sucrose) with protease inhibitor is added to the tube. The tissue is immediately minced in the tube with fine scissors while keeping the tube on ice. The biopsy tube is then placed in a small beaker with wet ice and immedi-ately homogenized with the PRO200 homogenizer with Multi-Gen adaptor and 5 mm generator at a medium setting (3) for 5 seconds. The tube remains on ice throughout the homogenization process. After homogenization, the sample is placed in an ice/water bath and incubated on a standard orbital shaker for a minimum of ten minutes, while other samples are processed.

To collect the cytosolic fraction, the total cell lysate is centrifuged in a microcentrifuge at 16,000×g for 30 minutes at 2-8° C. Without disturbing the pellet, the supernatant is transferred into a pre-chilled, 2 mL tube and kept on ice. The pellet contains the membrane, mitochondrial and nuclear cell fractions and is kept on ice for later processing. To each supernatant sample, 17 µL 20% Triton X-100 and 21 µL 10% CHAPS is added and mixed by pipetting up and down 5-8 times, minimizing the creation of bubbles, to produce a cytosolic stock lysate. For later use in a protein assay, dilutions of the stock lysate are made (for example, 20 µL of stock lysate+80 µL of 1×PBS=1:5 dilution; 10 µL of stock lysate+90 µL of 1×PBS=1:10 dilution) and stored at either −80° C. (for up to 5 days) or at 2-8° C. for same day use. Stock lysates are snap-frozen on dry ice and stored at −80° C.

To prepare the nuclear/mitochondrial fraction, the pellet is washed 2× by adding 350 µL MIM with protease inhibitors, pipetting up and down, centrifuging in a microcentrifuge at 16,000×g for 10 minutes at 2-8° C. Following each cen-trifugation, the supernatant is removed and discarded. The pellet is resuspended in 350 µL Buffer-A (0.5 M EDTA, CHAPS, 10% Triton X-100, 10×PBS) with protease inhibi-tors, vortexed for 10 seconds at maximum speed and then placed in an ice/water bath at 2-8° C. for 45 minutes on a standard orbital shaker (shake speed set at 4). Samples are vortexed every 20 minutes for 10 seconds while samples are shaking. Lysates are clarified by centrifugation in a micro-centrifuge at 16,000×g for 10 minutes at 2-8° C. The nuclear/mitochondrial stock lysate is transferred into a pre-chilled 2-mL tube and kept on ice. For later use in a protein assay, appropriate dilutions of the stock lysate are made (for example, 20 µL of stock lysate+80 µL of 1×PBS=1:5 dilution; 10 µL of stock lysate+90 µL of 1×PBS=1:10 dilution) and stored at either –80° C. (for up to 5 days) or at 2-8° C. for same day use. The nuclear/mitochondrial stock lysates are snap-frozen on dry ice and stored at –80° C.

The protein content of each sample can be determined, for example, using the bicinchoninic acid (BCA) according to standard procedures.

Example 3: Luminex Bead Multiplex Immunoassay Procedure

The immunoassays described herein were built on the Luminex xMAP multiplex technology platform using mag-netic bead capture. Washes were performed with a 96-well magnetic plate washer (ELx405, BioTek). During incuba-tion, the plates were placed on an orbital titer plate shaker (VWR International). Liquid handling was performed manu-ally with calibrated, adjustable, precision multichannel pipettes (Rainin 8-Channel). All assays were performed in 96-well plates (BioPlex, BioRad) at 25° C.±3° C. by adding 10 µL of blocking solution (Myriad RBM) and 30 µL of calibrator, control, or unknown sample. Antibody-coupled beads were sonicated for 5 seconds and then vortexed at medium speed for 10 to 20 seconds to disperse the beads, and 10 µL beads (250 beads/analyte/µL) were added to each well per analyte. Plates were protected from light (Black Microplate Lid, VWR) and incubated for 1 hour at 25° C.±3° C. with shaking. Plates were washed with wash solution (Myriad RBM), and then 40 µL of detection antibody-biotin conjugate was added and plates were incubated for an additional hour with shaking. After incubation with the antibody-biotin conjugate, 40 µL of R-phycoerythrin-la-beled streptavidin (Invitrogen) was added, and plates were incubated for 30 minutes with shaking. After a final wash, 100 µL of assay buffer was added to each well and plates were read on a Luminex 200 reader.

Example 4: Heterodimer Immunoassays

Figure 1:
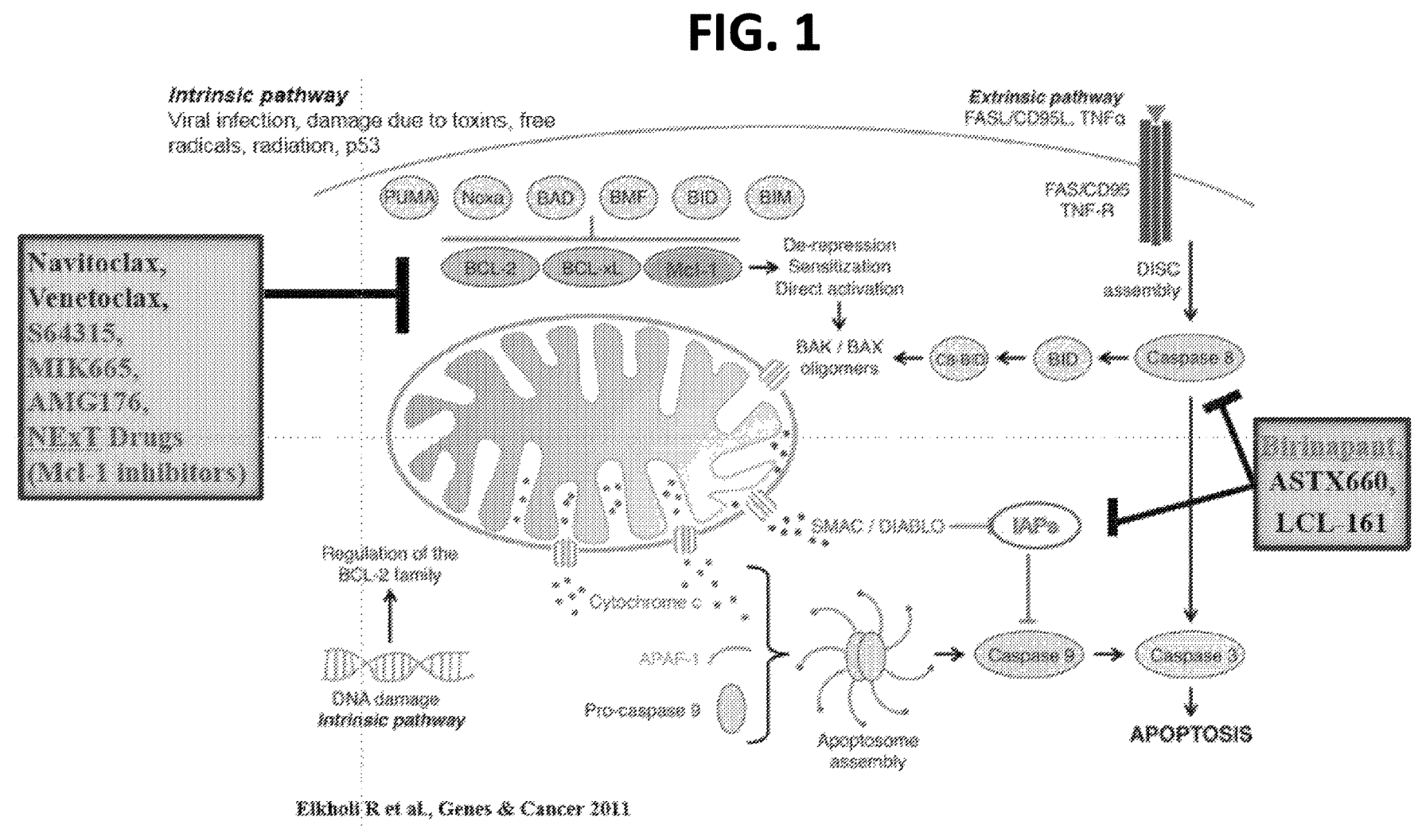

Cancer cells evade apoptosis by overexpressing anti-apoptotic proteins such as Mcl-1, Bcl-xL and Bcl-2. Within cells, anti-apoptotic proteins exist primarily as complexed heterodimers with pro-apoptotic proteins such as BAK, BAX, Bad, BIM, Puma or Noxa (FIG. 1). This example describes sandwich immunoassays to detect heterodimers of BIM-Mcl-1, BIM-Bcl-2, BIM-Bcl-xL, and BAX-BAK, and use of the immunoassays to study the levels of these heterodimers in different cancer cell lines. Quantitative measurements of heterodimeric forms of BIM and BAX proteins in tumor lysates represents a novel approach since it evaluates a pathway based on alterations in protein dynamics, instead of the static levels of individual proteins.

Figure 2A:
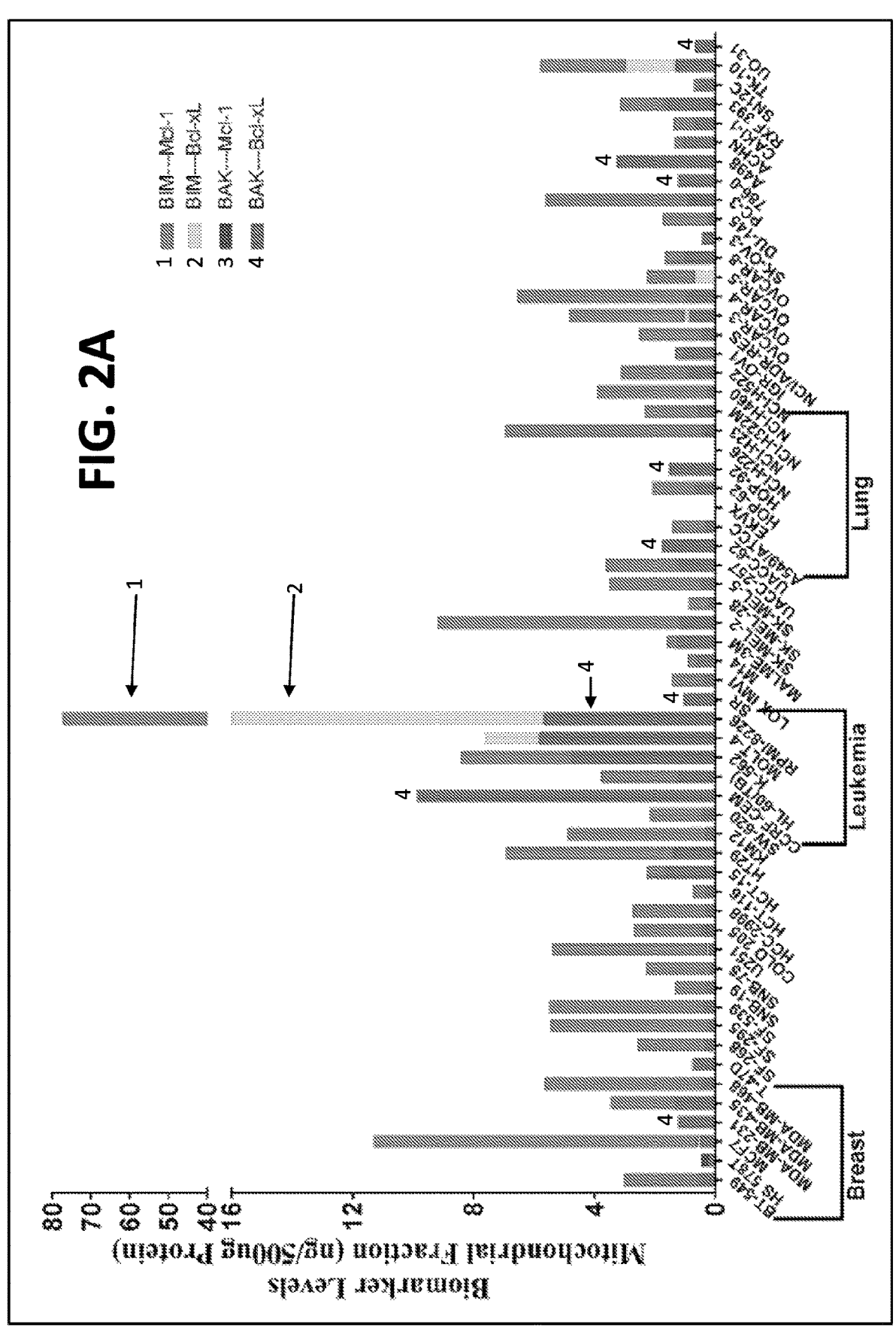
FIGS. 2A-2B are a pair of graphs showing the level of Bcl-2 family heterodimers in cancer cells.
Figure 2B:
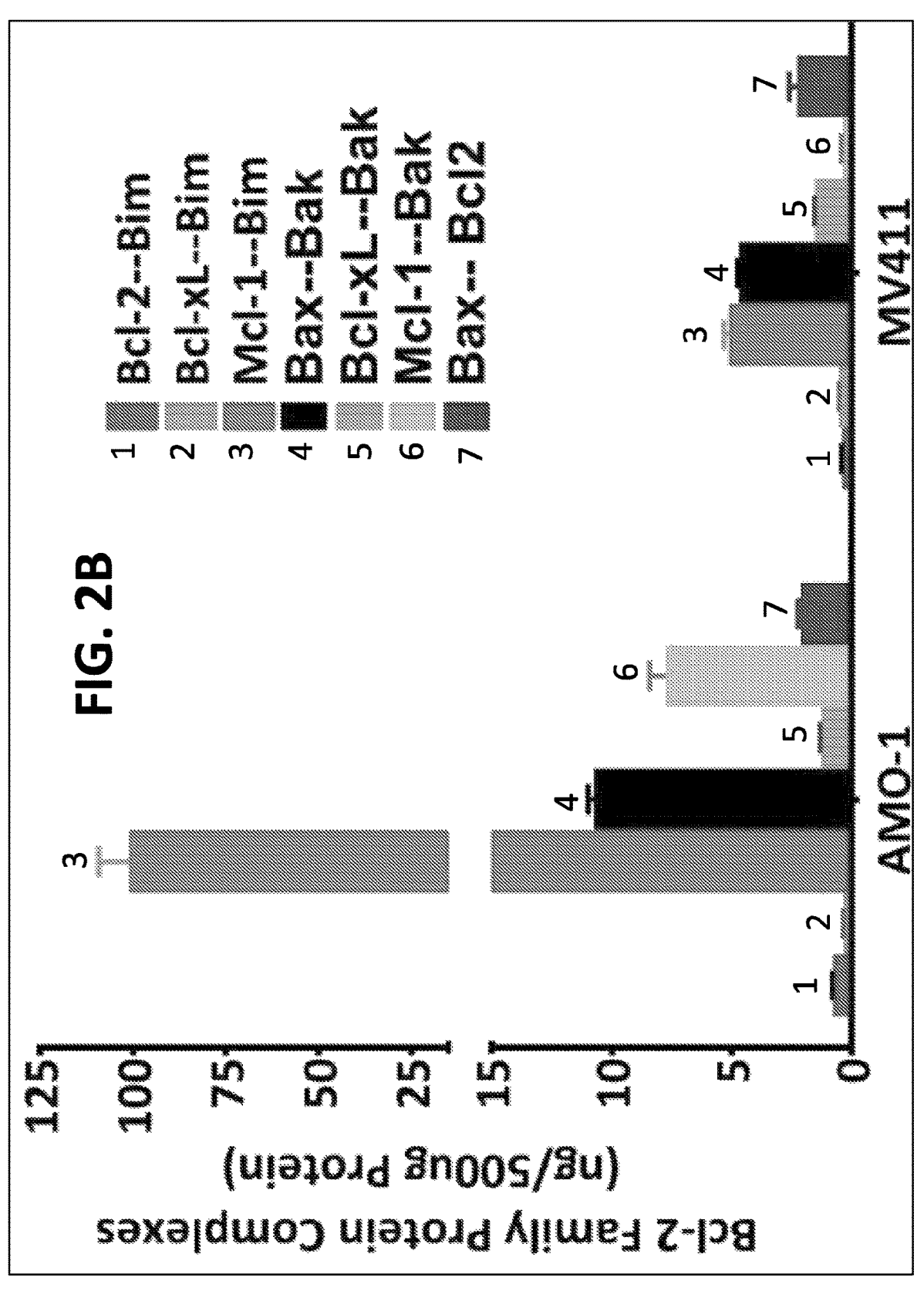

A heterodimer immunoassay was performed to determine the level of each heterodimer in a panel of cancer cells lines. As shown in FIG. 2A, heterodimer levels varied amongst the different cancer cell lines tested. In cell lines that are sensitive to Mcl-1 inhibitor, the majority of Mcl-1 was bound to BIM (FIG. 2B).

Figure 3A:
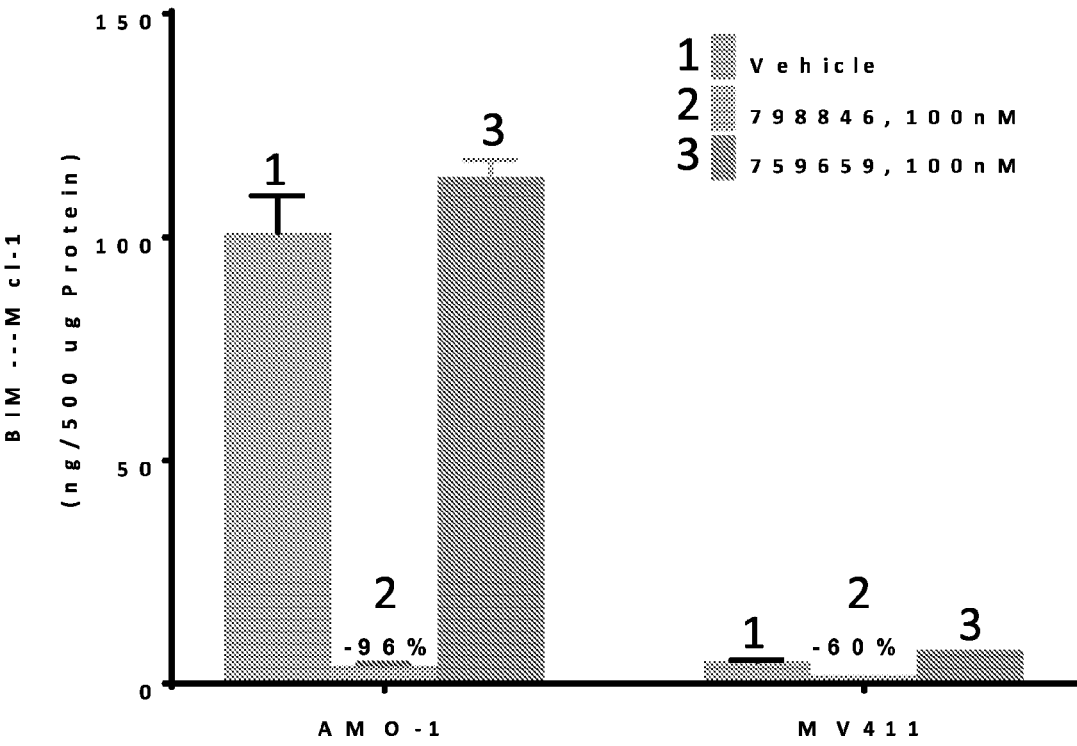
FIGS. 3A-3C are graphs showing heterodimer levels in AMO-1 and MV411 cancer cell lines in the presence and absence of a BH3 mimetic.
Figure 3B:
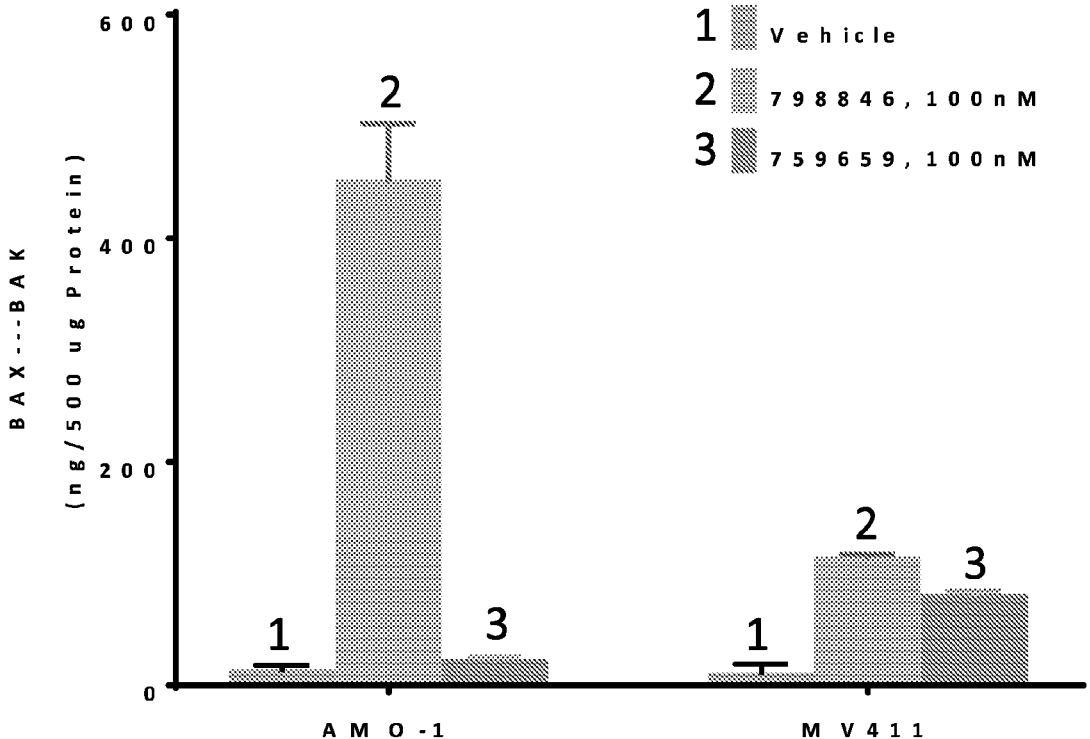
Figure 3C:
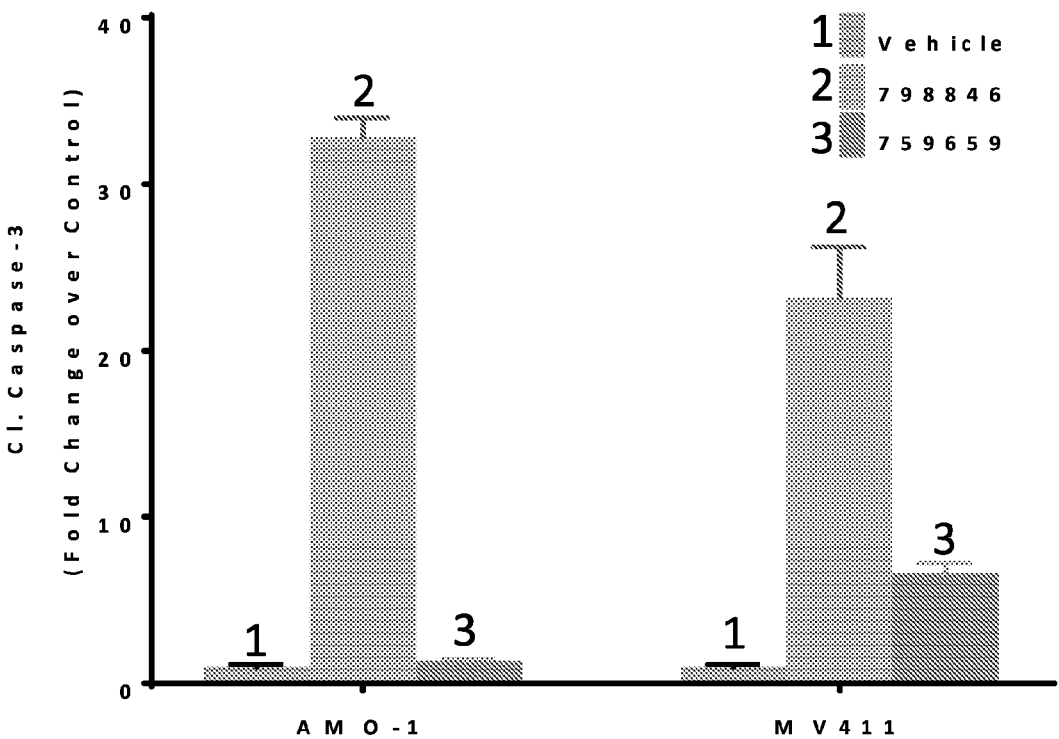

A recent study identified the sensitivity of a panel of 11 cell lines representative of human lymphomas and chronic myeloid leukemia to Mcl-1 inhibitor S63845 (Kotschy et al., *Nature* 538(7626): 477-482, 2016). Among them, the AMO-1 cell line was highly sensitive (IC50<0.1 µM) to S63845. Intravenous injection of this drug exerted dose-dependent anti-tumor activity in AMO1 xenografts. In vivo, S63845 showed less potent activity in the MV4-11 human AML xenograft model. In view of this data, an immunoassay was performed to determine BIM- and BAX-containing heterodimer levels in vitro in AMO-1 and Mv411 cell lines treated with S63845 and Bcl-xL inhibitor novitoclax. FIG. 3A shows that BIM-Mcl-1 concentrations were 80- to 90-fold higher in AMO-1 cells, as compared to Mv411 cells. In addition, BIM-Mcl-1 levels were decreased by S63845, whereas BIM-Mcl-1 levels were largely unaffected by novi-toclax). Inhibition of BIM-Mcl-1 complexes caused increased downstream activation of BAX-BAK heterodimer formation in the mitochondrial fraction (FIG. 3B). Further-more, increased activation of BAX-BAK heterodimer led to generation of cleaved caspase-3 (FIG. 3C), which has been linked to commitment to apoptotic cell death. These results demonstrate that measurement of BIM and BAX heterodi-mers can be used to determine the sensitivity of cancer cells to a BH3 mimetic, and sheds light on the mechanism of drug action in cancer cells.

Figure 4A:
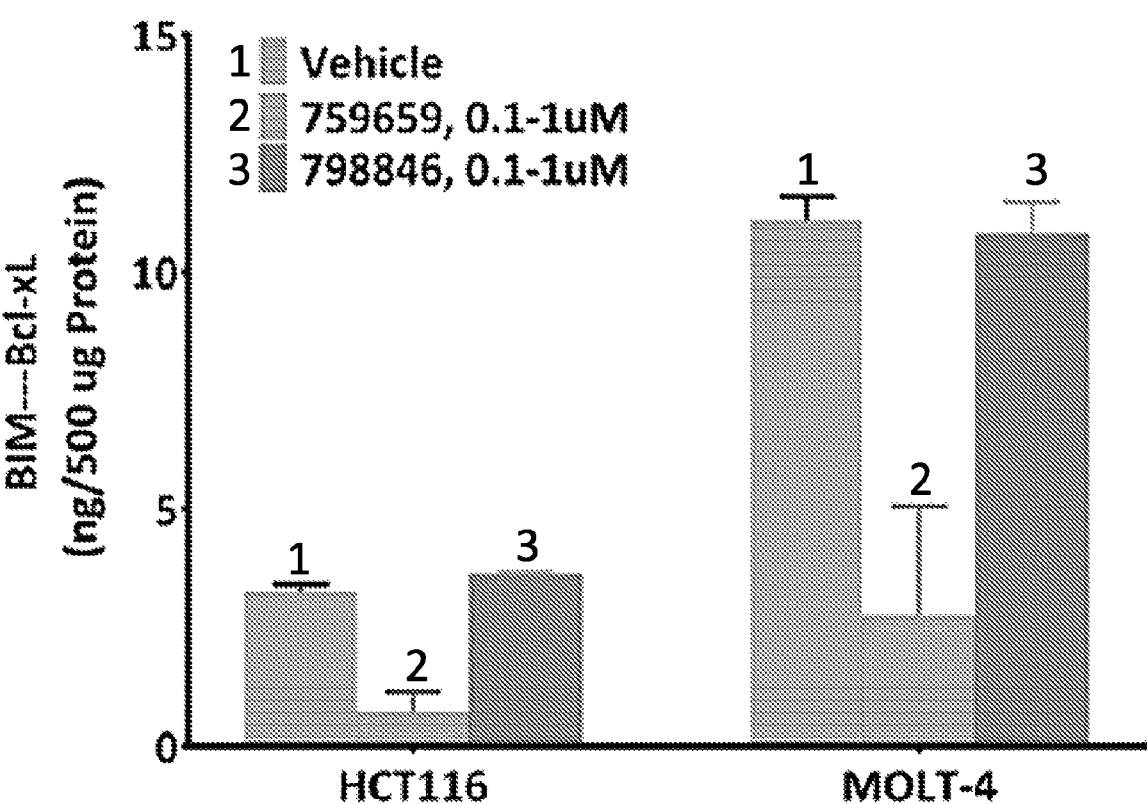
FIGS. 4A-4D are graphs showing heterodimer levels in untreated and BH3 mimetic-treated tumor cells.
Figure 4B:
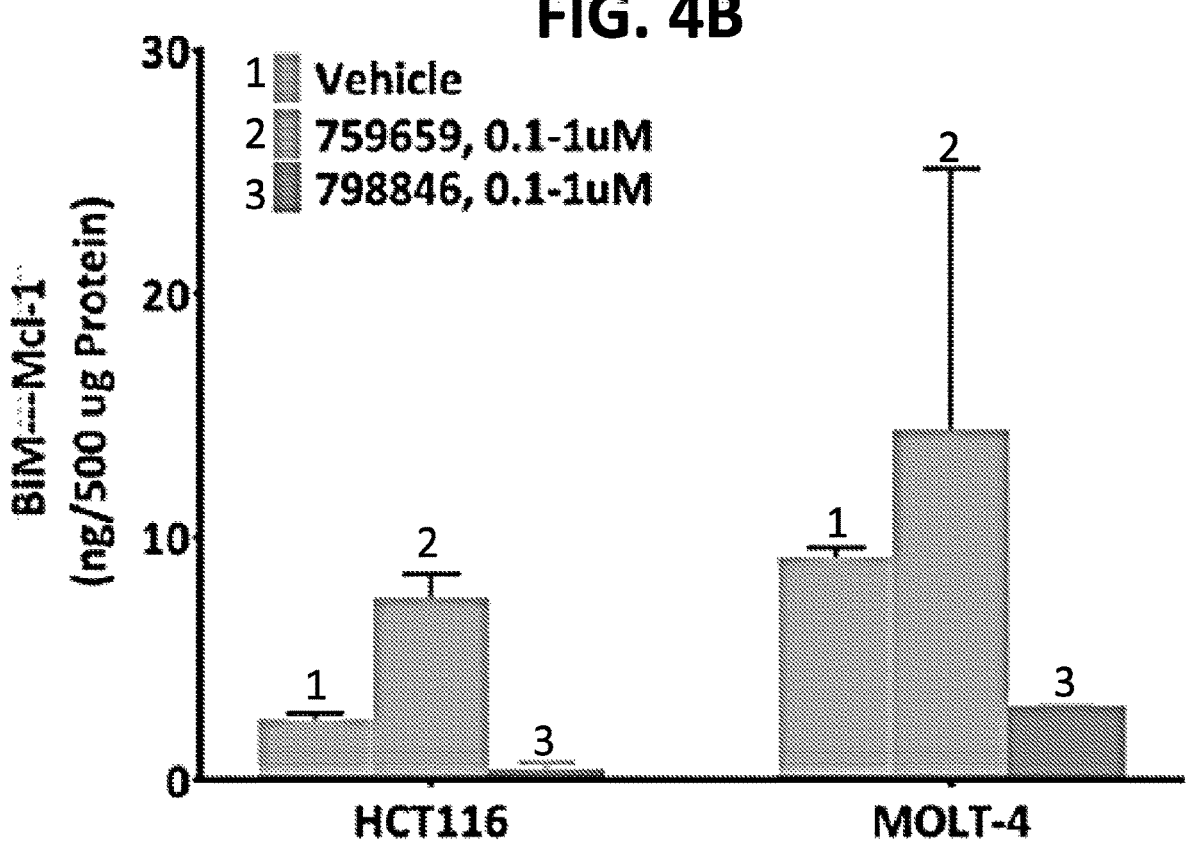
Figure 4C:
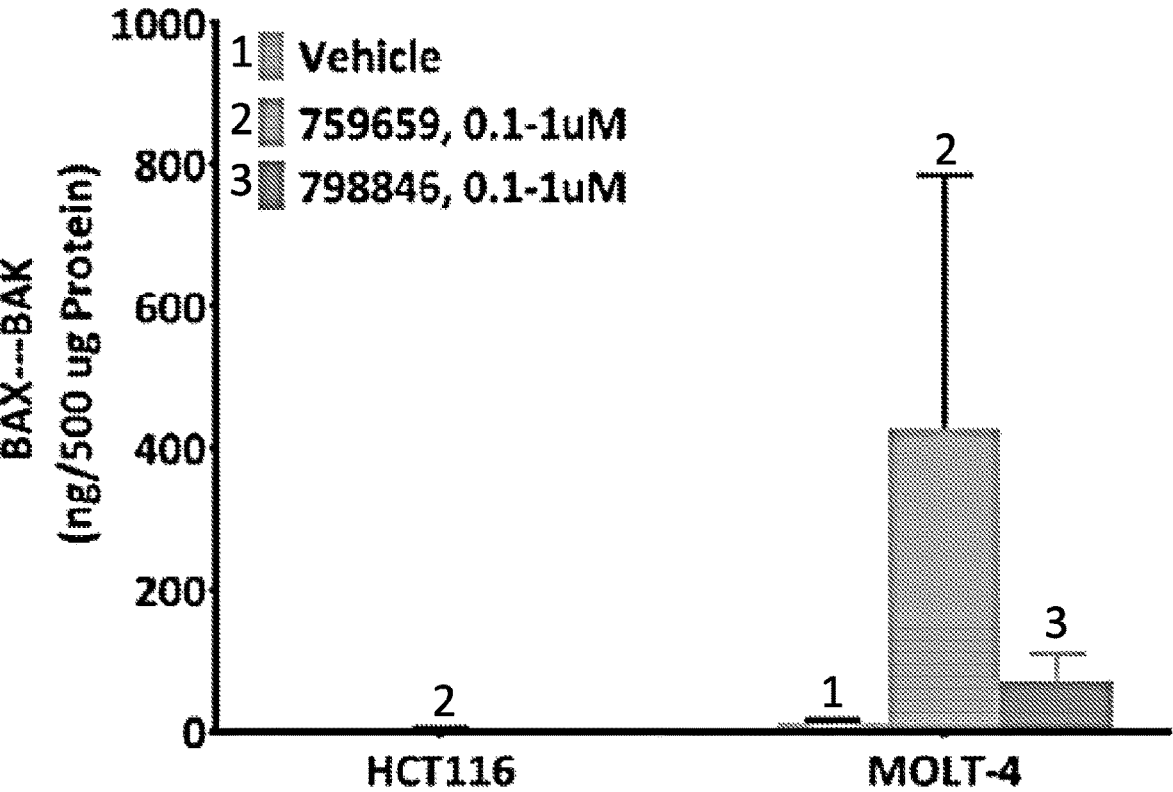
Figure 4D:
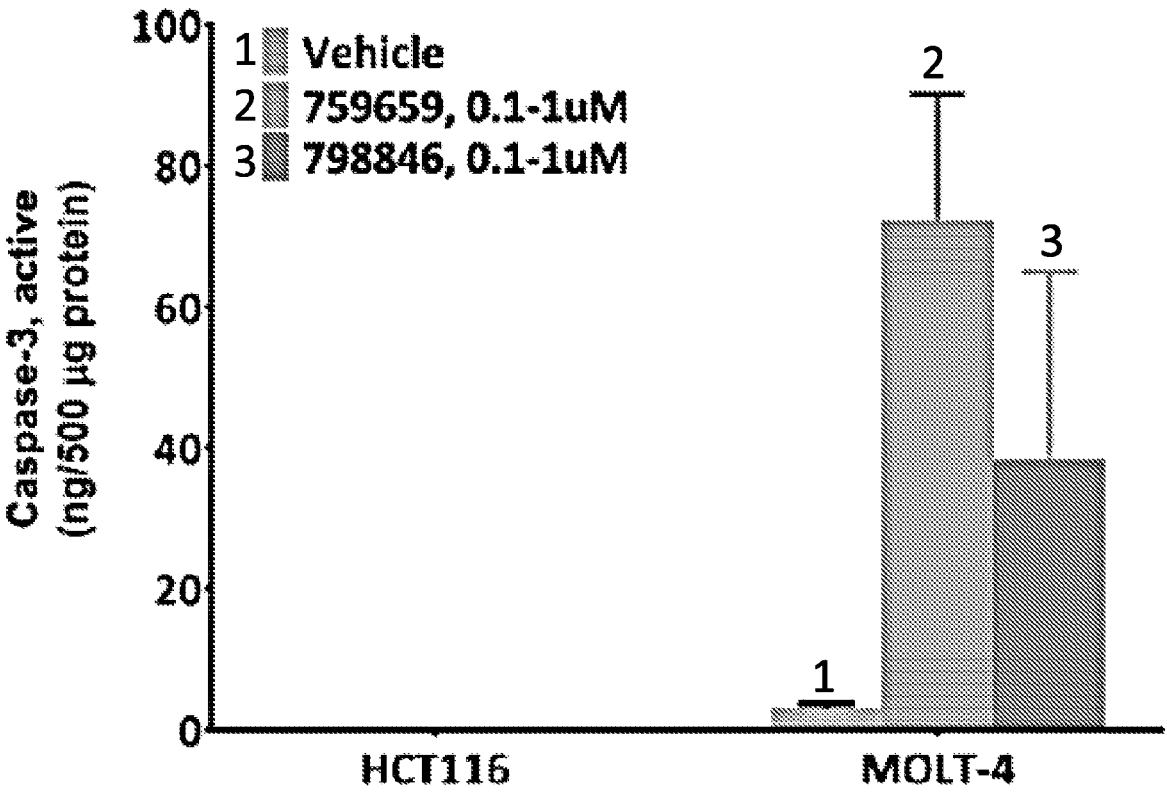

Further studies were conducted to evaluate the effect of BH3 mimetics on Bcl-2 family heterodimer levels and induction of apoptosis. Levels of BIM-Bcl-xL, BIM-Mcl-1 and BAX-BAK heterodimers in HCT116 and MOLT-4 can-cer cell lines treated with novitoclax (759659) or S63845 (798846) were analyzed. As shown in FIG. 4A, BIM-Bcl-xL levels were only disrupted by novitoclax, a known Bcl-xL inhibitor, but not by Mcl-1 inhibitor S63845. Similarly, BIM-Mcl-1 levels were only suppressed by S63845 (FIG. 4B). Novitoclax treatment resulted in increased BIM-Mcl-1 levels due to re-equilibrium of BIM and Bcl-xL/Mcl-1 (FIG. 4B). Both drugs increased downstream effector BAX-BAK levels (FIG. 4C), and increased activation of cleaved caspase-3 (FIG. 4D).

Figure 5B:
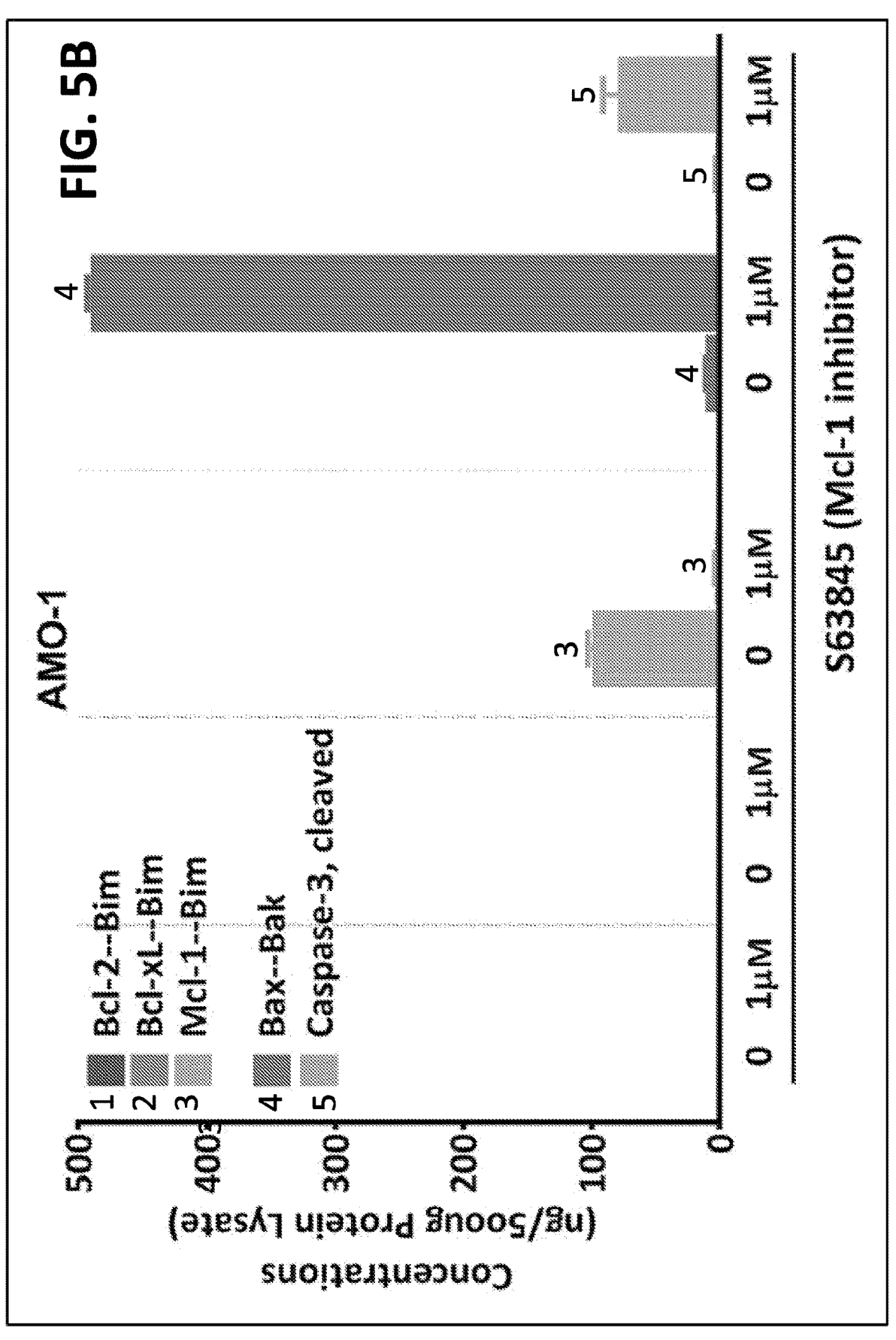
Figure 5C:
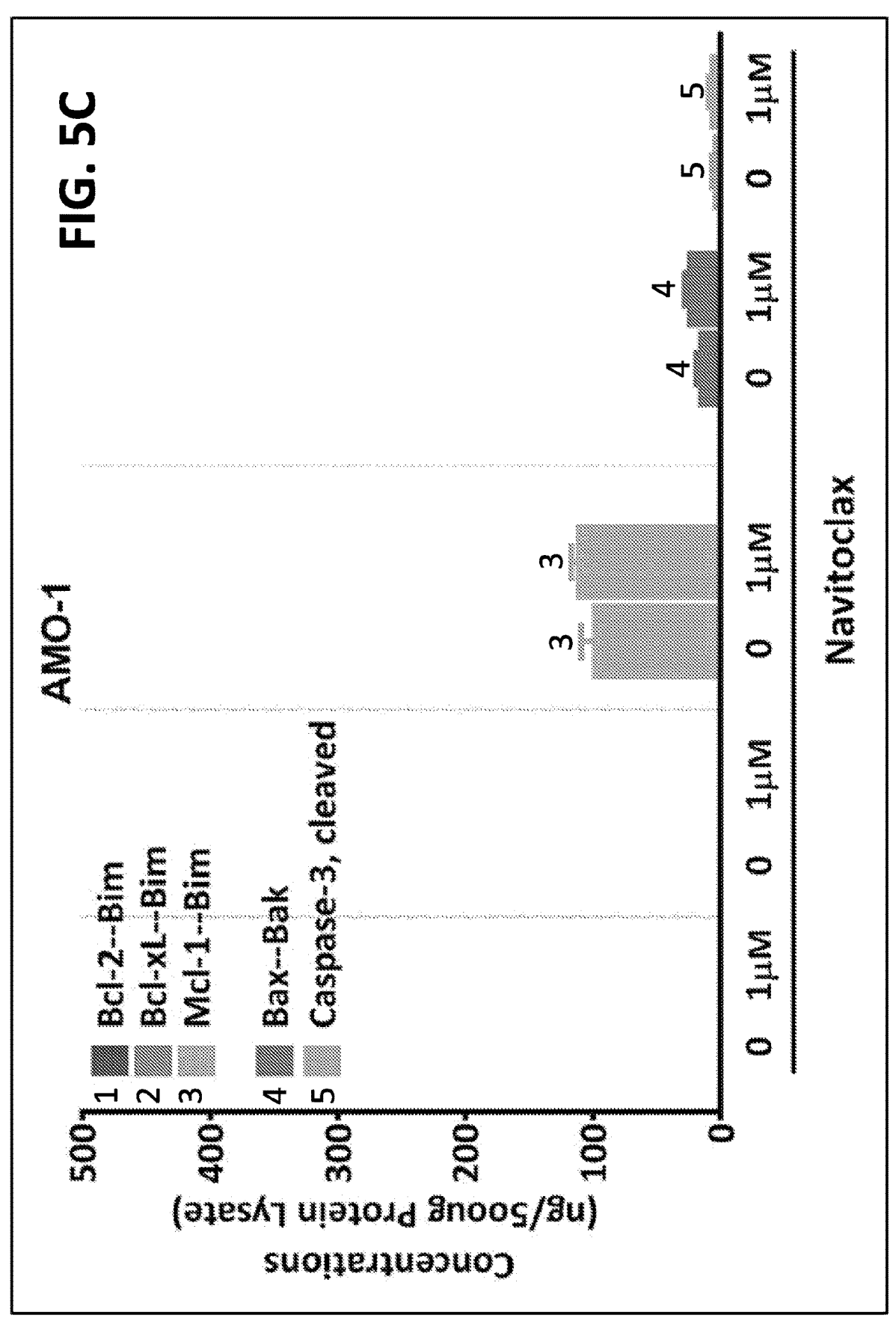
Figure 5D:
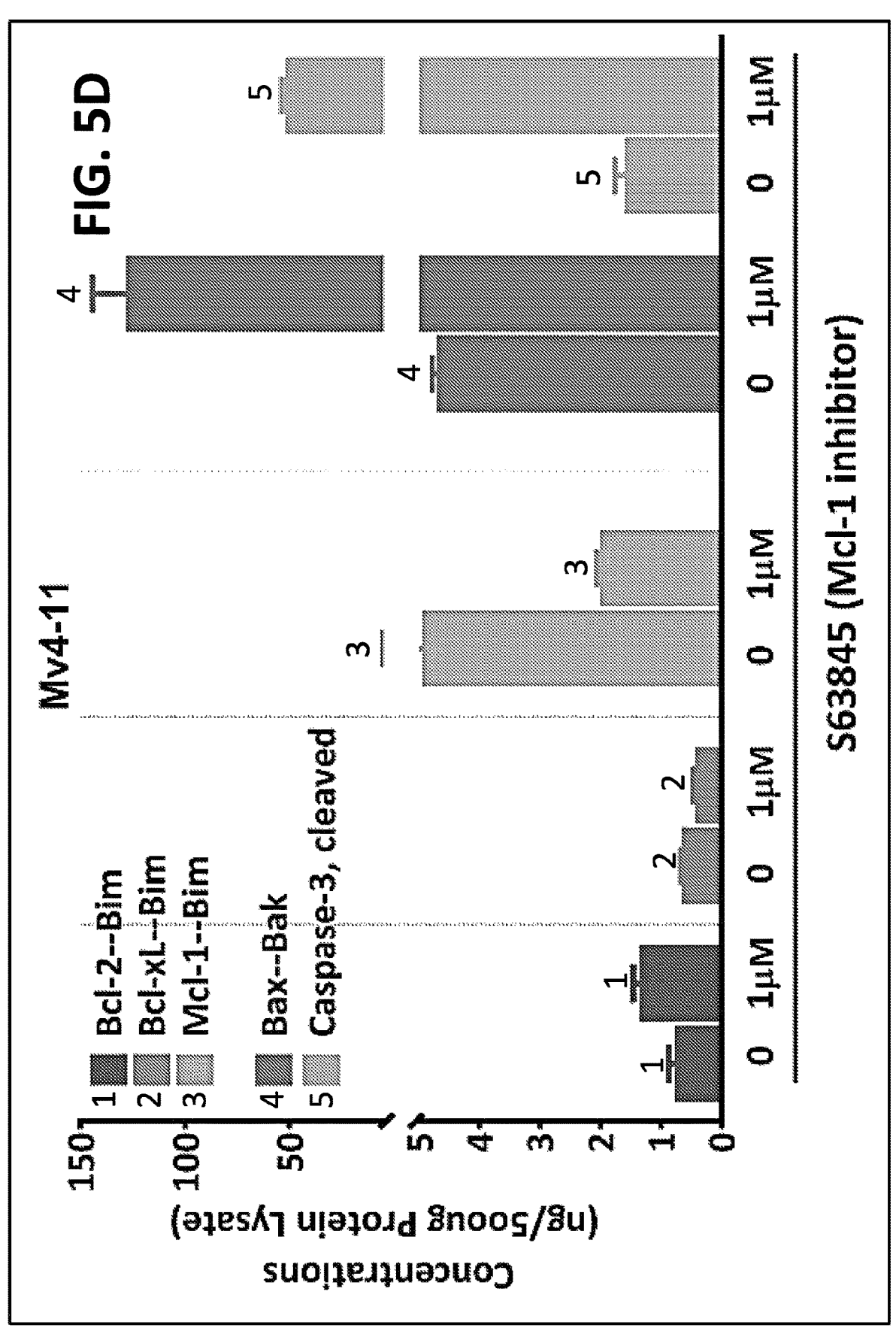
Figure 5E:
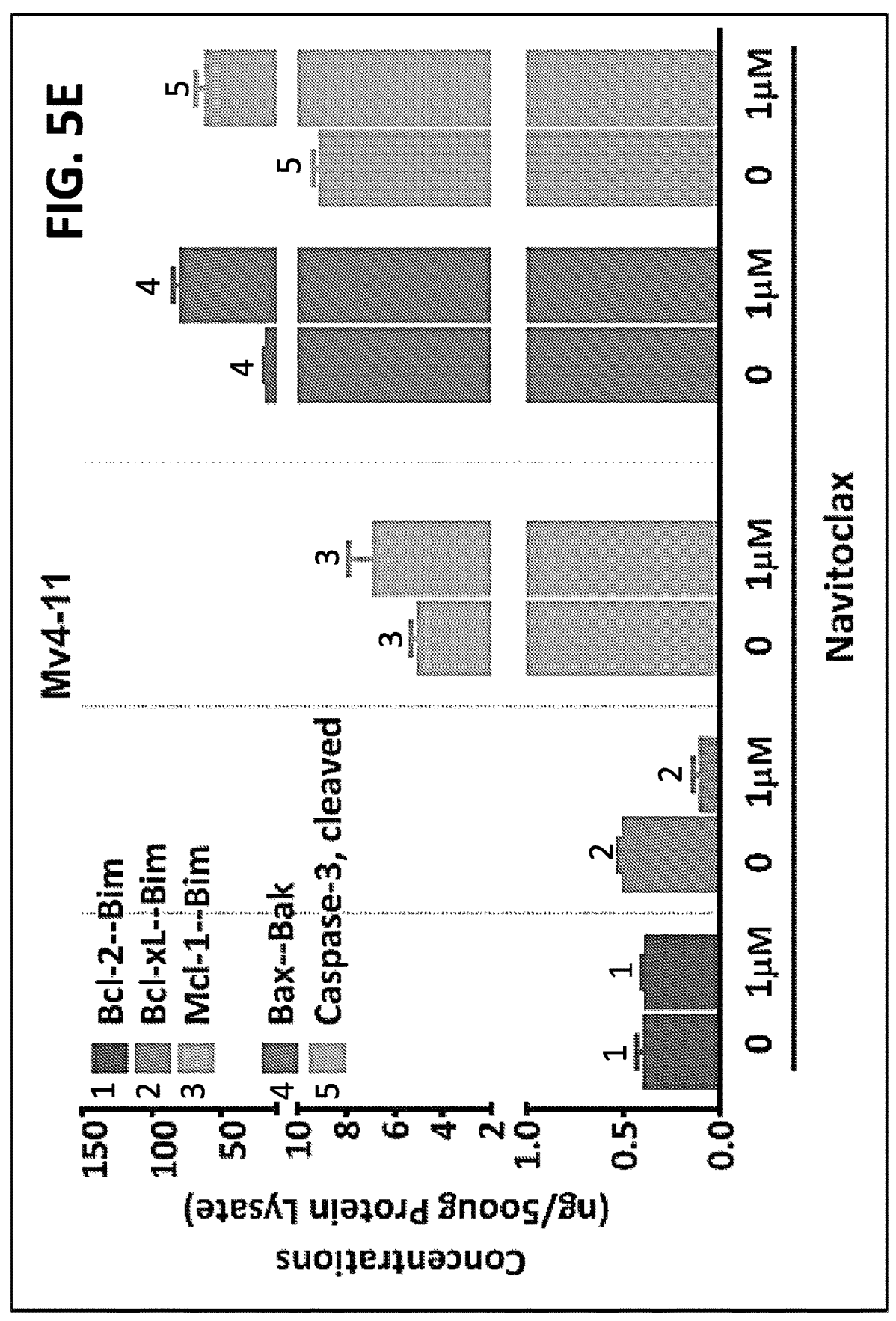

Similar studies were performed in AMO-1 plasmacytoma cells and Mv4-11 acute myeloid leukemia cells. AMO-1 and Mv4-11 cells were either untreated or treated with 1 M S63845 or novitoclax. Cell lysates were prepared and the concentration of BIM-Bcl-xL, BIM-Mcl-1, BIM-Bcl-2 and BAX-BAK heterodimers was determined using the het-erodimer immunoassay. The level of cleaved caspase-3 was also determined. Treatment of AMO-1 cells with S63845 led to a decrease in BIM-Mcl-1 heterodimers and an increase in both BAX-BAK heterodimers and cleaved caspase-3 (FIG. 5B), whereas treatment with novitoclax did not lead to a significant increase in caspase-3 cleavage due to the lack of BIM-Bcl-xL heterodimeric complexes in AMO-1 cells (FIG. 5C). Treatment of Mv4-11 cells with S63845 led to a significant decrease in BIM-Mcl-1 heterodimers and a sig-nificant increase in both BAX-BAK heterodimers and cleaved caspase-3 (FIG. 5D). Treatment of Mv4-11 cells with novitoclax led to a decrease in BIM-Bcl-xL heterodi-meric complexes and an increase in BIM-Mcl-1, BAX-BAK and cleaved caspase-3 (FIG. 5E).

Taken together, these studies demonstrate that: (1) differ-ent BH3 mimetics disrupt specific BIM heterodimers and their measurement provides direct evidence of drug activity in tumor cells; and (2) effectiveness of a BH3 mimetic drug depends on the BIM heterodimer levels in a cancer cell.

Thus, BIM levels can be used to select the most potent BH3 mimetic or a combination of mimetics to induce apoptotic cell death.

Example 5: Bcl-2 Heterodimer Complexes in Hematological Malignancy

This example describes the characterization of Bcl-2 family heterodimers present in a model multiple myeloma (AMO-1), a model of acute myeloid leukemia (AML) (MV411) and in blood or bone marrow of patients with chronic lymphocytic leukemia (CLL). This example also describes the effect of treatment with BH3 mimetics on heterodimer composition.

Figure 6A:
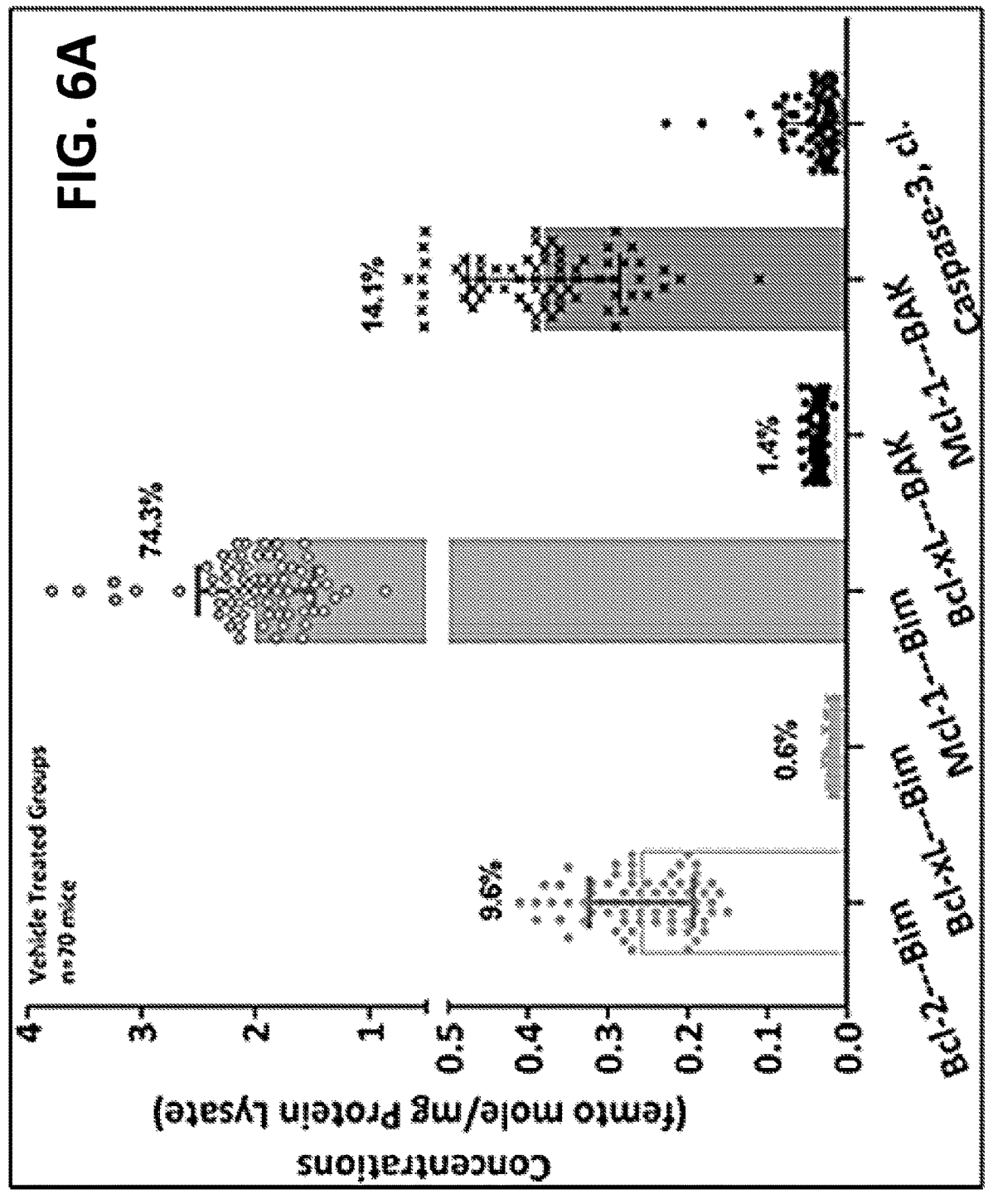
FIGS. 6A-6B are graphs showing the levels of major pro-survival proteins in two hematological malignancy preclinical models. Levels of BIM complexes were measured in xenograft tumor lysates from multiple myeloma (MM) model AMO-1 (FIG. 6A) and acute myeloid leukemia (AML) model MV411 (FIG. 6B). Each bar represents the average of 70 xenograft tumors each collected from different mice bearing AMO-1 and MV411 tumors. These models represent a subset of patients with MM and AML who are known to have dependency on Bcl-2, Bcl-xL or Mcl-1 proteins.
Figure 6B:
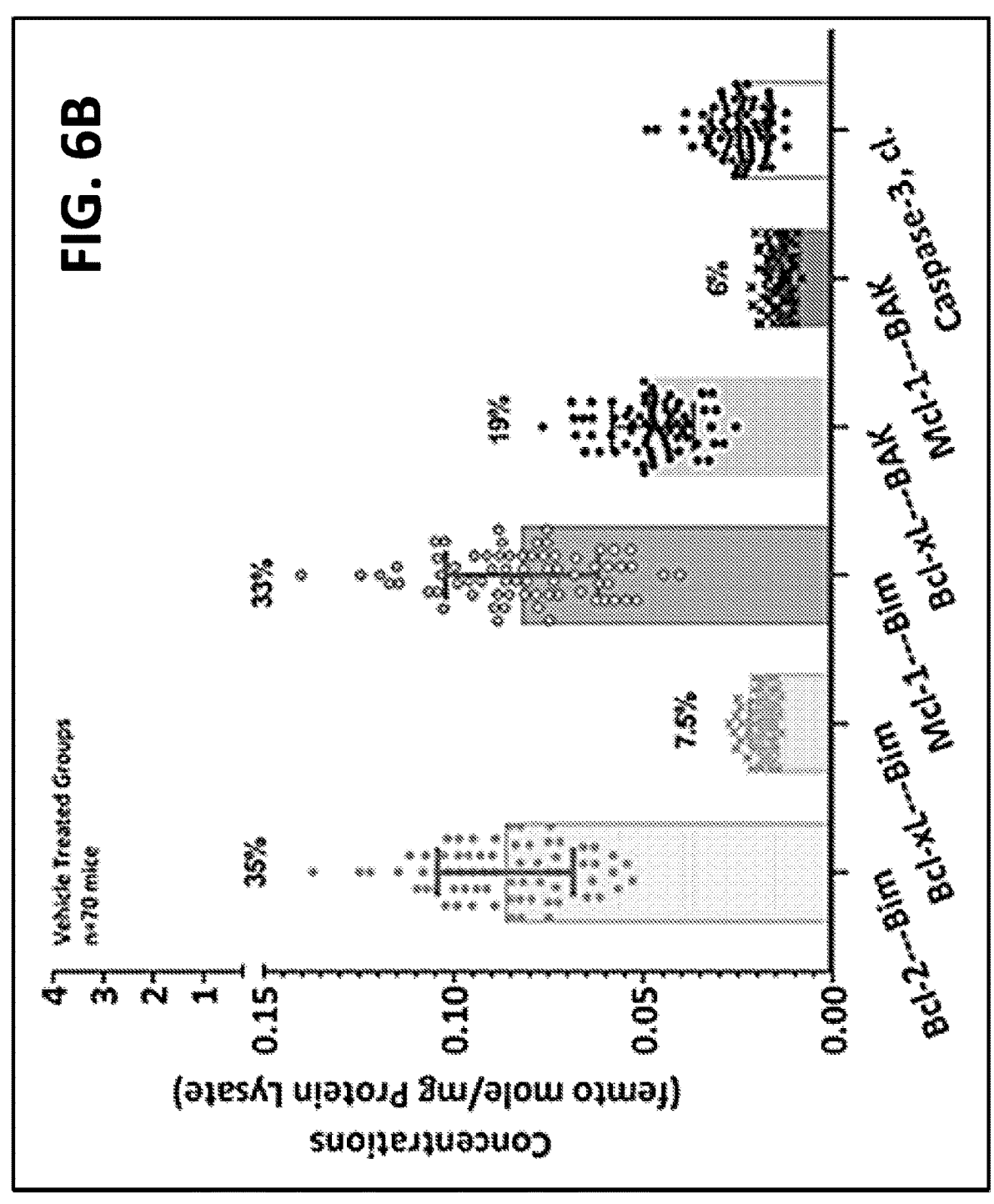

Heterodimer complexes were measured in AMO-1 and MV11 xenograft tumor lysates using the immunoassay described in Examples 3 and 4. AMO-1 is a plasmacytoma (multiple myeloma) model and MV411 is a model of AML. The levels of BIM-Bcl-2, BIM-Bcl-xL, BIM-Mcl-1, Bcl-xL-BAK and Mcl-1-BAK in AMO-1 and MV411 lysates are shown in FIG. 6A and FIG. 6B, respectively. The level of cleaved caspase-3 was also measured. Each bar represents the average of 70 xenograft tumors each collected from different mice bearing AMO-1 and MV411 tumors. These models represent a subset of patients with MM and AML who are known to have dependency on Bcl-2, Bcl-xL or Mcl-1 proteins. Heterodimer composition was also measured in blood or bone marrow samples of 11 patients with CLL. As shown in FIG. 6C, Similar heterodimer profiles were identified in samples from all 11 patients with CLL.

These data demonstrated differences in the levels of pro-survival proteins and how they are complexed. Identifying this dependency at the protein level allows for selection of an appropriate drug to match with tumor survival mechanisms.

Figure 7A:
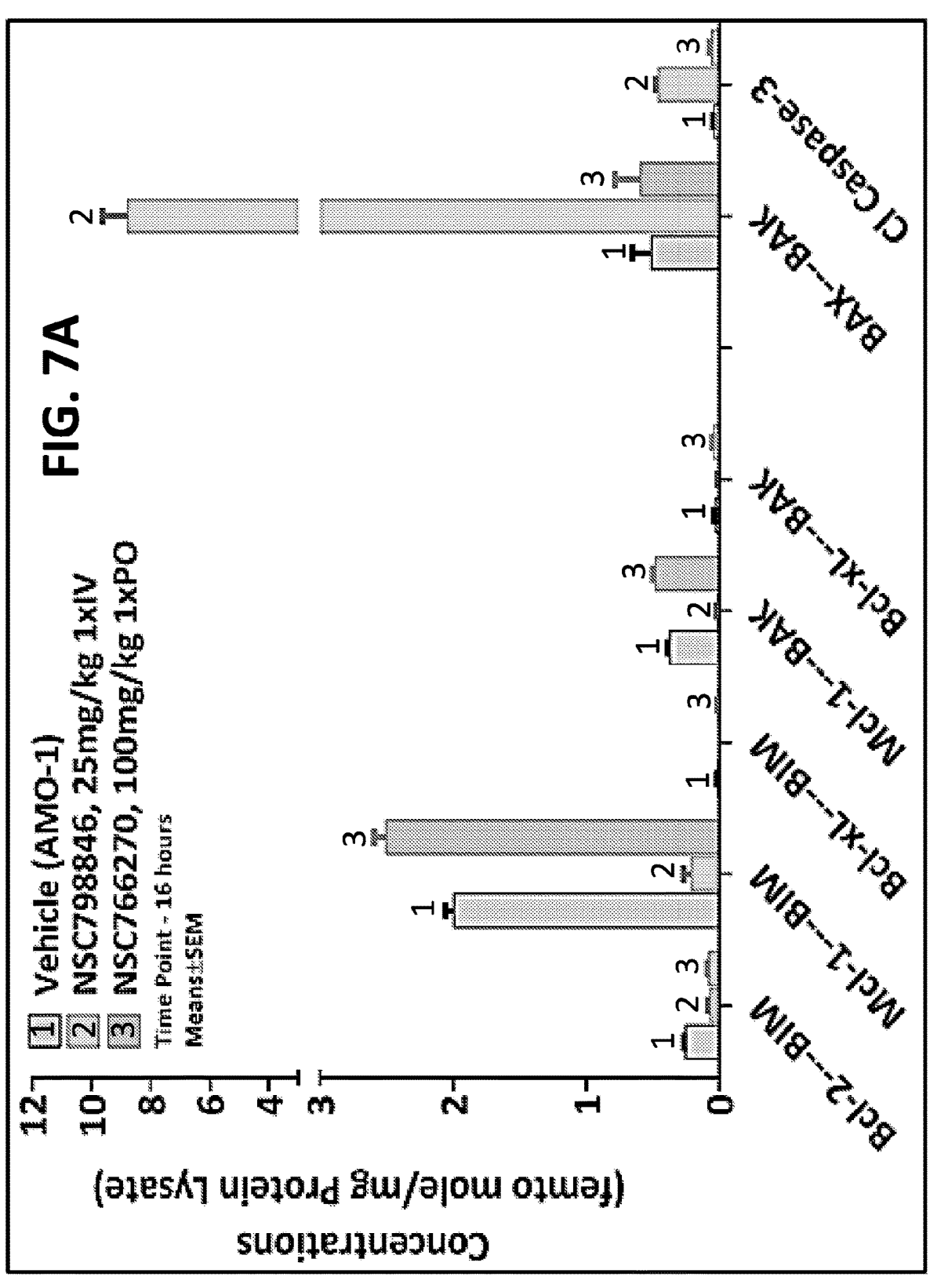
FIGS. 7A-7B are graphs showing heterodimer response after treatment of two preclinical models with BH3 mimetics NSC798846 (an Mcl-1 inhibitor) and NSC766270 (a Bcl-2 inhibitor).
Figure 7B:
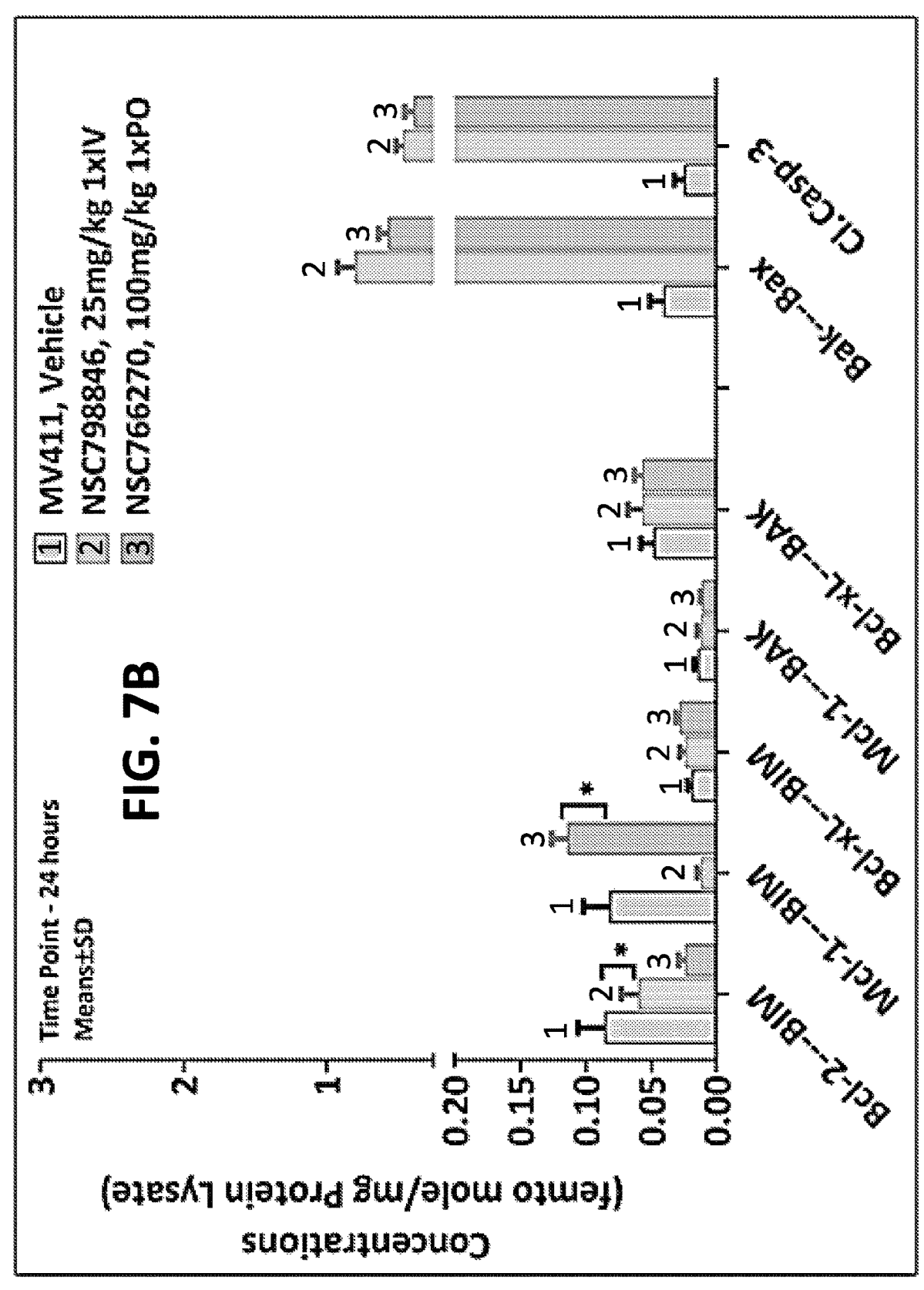

The effect of two different BH3 mimetics on heterodimer composition in the AMO-1 and MV411 models was next evaluated. Mice bearing AMO-1 or MV411 xenograft tumors were administered 25 mg/kg of NSC798846 (an Mcl-1 inhibitor) intravenously or 100 mg/kg of NSC766270 (a Bcl-2 inhibitor) orally. Heterodimer complexes were measured in tumor lysates prepared from AMO-1 mice 16 hours after treatment and from MV411 mice 24 hours after treatment. As shown in FIG. 7A, multiple myeloma model AMO-1 showed Mcl-1 dependency and treatment with Bcl-2 inhibitor NSC766270 was ineffective because BIM released from disruption of Bcl-2-BIM complexes was largely bound to Mcl-1 and did not initiate BAK-BAX oligomerization (mitochondrial poration marker), subsequent caspase-3 activation and cell death. The disruption of Bcl-2-BIM by Mcl-1 inhibitor NSC798846 was due to overall degradation of BIM. As shown in FIG. 7B, AML model MV411 showed Mcl-1 or Bcl-2 inhibitors were equally effective in disrupting the balance of BIM complexes and initiating caspase-3 activation and cell death. The differences in timepoints selected for biomarker response was based on different pharmacokinetics of NSC798846 and NSC766270 in mice.

FIGS. 7C and 7D depict the action of two BH3 mimetics on the disruption of major pro-survival protein complexes that trigger mitochondrial activation of caspase-3 and cell death. Taken together, these data demonstrate that the heterodimer assays disclosed herein can be used to identify patients who will respond to a drug targeting the apoptosis pathway but also provide an indication of the effectiveness of a particular drug targeting the apoptosis pathway and predict anti-tumor efficacy.

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims.

---

The invention claimed is:

1. A method of detecting at least two different Bcl-2 family heterodimeric protein complexes in a biological sample, comprising:

providing a cell lysate of a biological sample that comprises cells; and detecting the presence of the at least two different Bcl-2 family heterodimeric protein complexes in the cell lysate, wherein each heterodimeric protein complex comprises a first protein and a second protein, and wherein detecting each heterodimeric protein complex comprises:

providing an antibody specific for the first protein bound to a solid support;

providing a detection antibody specific for the second protein, wherein the detection antibody is covalently attached to a detectable label;

contacting the cell lysate with the antibody-bound solid support and the detection antibody; and detecting the presence of the detection antibody, thereby detecting the Bcl-2 family heterodimeric complex in the biological sample, wherein the at least two different Bcl-2 family heterodimeric protein complexes comprise:

BIM-Bcl-2 and BIM-Bcl-xL;

BIM-Bcl-2 and BAK-BAK;

BIM-Bcl-xL and BIM-Mcl-1;

BIM-Bcl-xL and BAK-BAK; or

BIM-Mcl-1 and BAX-BAK.

2. The method of claim 1, wherein the biological sample comprises a tissue sample, a biopsy sample, a fine-needle tumor aspirate, a bone marrow aspirate or a blood sample.

3. The method of claim 1, wherein the solid support comprises a bead, a tissue culture plate or an affinity column.

4. The method of claim 1, wherein the detectable label comprises biotin, a peptide sequence tag, a fluorescent label, a luminescence label, an enzyme, a nucleotide sequence tag, a nanoparticle, or a combination thereof.

5. The method of claim 1, comprising detecting at least three different heterodimeric protein complexes, wherein the at least three different heterodimeric protein complexes comprise:

BIM-Bcl-2, BIM-Bcl-xL and BIM-Mcl-1;

BIM-Bcl-2, BIM-Bcl-xL and BAX-BAK;

BIM-Bcl-xL, BIM-Mcl-1 and BAX-BAK; or

BIM-Bcl-2, BIM-Mcl-1 and BAX-BAK.

6. The method of claim 5, comprising:

detecting BIM-Bcl-2, BIM-Bcl-xL and BIM-Mcl-1 heterodimeric protein complexes; or detecting BIM-Bcl-2, BIM-Bcl-xL, BIM-Mcl-1 and BAX-BAK heterodimeric protein complexes.

7. The method of claim 1, further comprising determining the concentration of the at least two different heterodimeric protein complexes in the cell lysate, comprising comparing the amount of the heterodimeric protein complexes in the cell lysate with the amount of total protein present in the cell lysate.

8. The method of claim 1, wherein the biological sample is from a subject diagnosed with cancer, and the method further comprises treating the subject with a drug targeting the apoptosis pathway.

9. The method of claim 8, wherein the drug targeting the apoptosis pathway is selected from the group consisting of a BH3 mimetic, a BAX/BAK modulator, an inhibitor of apoptosis protein (IAP) inhibitor, a CDK inhibitor, and a death receptor pathway inhibitor.

10. The method of claim 3, wherein the bead is a glass bead, a plastic bead or a magnetic bead.

11. The method of claim 9, wherein the BH3 mimetic is an inhibitor of Mcl-1.

12. The method of claim 9, wherein the BH3 mimetic is an inhibitor of Bcl-2 or Bcl-xL.

13. The method of claim 9, wherein the BH3 mimetic is an inhibitor of Bcl-2 and Bcl-xL.

14. The method of claim 8, wherein the cancer is a solid tumor.

15. The method of claim 8, wherein the cancer is a hematopoietic cancer.

16. A method of detecting at least two different Bcl-2 family heterodimeric protein complexes in a biological sample that comprises cells, wherein the biological sample comprises a tissue sample, a biopsy sample, a fine-needle tumor aspirate, a bone marrow aspirate or a blood sample, comprising:

providing a cell lysate of the biological sample; and detecting the presence of the at least two different Bcl-2 family heterodimeric protein complexes in the cell lysate, wherein each heterodimeric protein complex comprises a first protein and a second protein, and wherein detecting each heterodimeric protein complex comprises:

providing an antibody specific for the first protein bound to a solid support;

providing a detection antibody specific for the second protein;

contacting the cell lysate with the antibody-bound solid support and the detection antibody; and detecting the presence of the detection antibody, thereby detecting the Bcl-2 family heterodimeric complex in the biological sample, wherein the at least two different Bcl-2 family heterodimeric protein complexes comprise:

BIM-Bcl-2 and BIM-Bcl-xL;

BIM-Bcl-2 and BAK-BAK;

BIM-Bcl-xL and BIM-Mcl-1;

BIM-Bcl-xL and BAK-BAK; or

BIM-Mcl-1 and BAX-BAK.

17. The method of claim 16, comprising detecting at least three different heterodimeric protein complexes, wherein the at least three different heterodimeric protein complexes comprise:

BIM-Bcl-2, BIM-Bcl-xL and BIM-Mcl-1;

BIM-Bcl-2, BIM-Bcl-xL and BAX-BAK;

BIM-Bcl-xL, BIM-Mcl-1 and BAX-BAK; or

BIM-Bcl-2, BIM-Mcl-1 and BAX-BAK.

18. The method of claim 17, comprising:

detecting BIM-Bcl-2, BIM-Bcl-xL and BIM-Mcl-1 heterodimeric protein complexes; or detecting BIM-Bcl-2, BIM-Bcl-xL, BIM-Mcl-1 and BAX-BAK heterodimeric protein complexes.

19. The method of claim 16, wherein the biological sample is from a subject diagnosed with cancer, and the method further comprises treating the subject with a drug targeting the apoptosis pathway.

20. The method of claim 19, wherein the drug targeting the apoptosis pathway is selected from the group consisting of a BH3 mimetic, a BAX/BAK modulator, an inhibitor of apoptosis protein (IAP) inhibitor, a CDK inhibitor, and a death receptor pathway inhibitor.

* * * * *

SEQUENCE LISTING

```
<160> NUMBER OF SEQ ID NOS: 5

<210> SEQ ID NO 1
<211> LENGTH: 442
<212> TYPE: PRT
<213> ORGANISM: Artificial Sequence
<220> FEATURE:
<223> OTHER INFORMATION: Fusion protein (BIM-Bcl-2)

<400> SEQUENCE: 1

Gly Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Glu Gly Asn His
        35                  40                  45

Gly Gly Glu Gly Asp Ser Cys Pro His Gly Ser Pro Gln Gly Pro Leu
    50                  55                  60

Ala Pro Pro Ala Ser Pro Gly Pro Phe Ala Thr Arg Ser Pro Leu Phe
65                  70                  75                  80

Ile Phe Met Arg Arg Ser Ser Leu Leu Ser Arg Ser Ser Ser Gly Tyr
                85                  90                  95

Phe Ser Phe Asp Thr Asp Arg Ser Pro Ala Pro Met Ser Cys Asp Lys
                100                 105                 110
```

-continued

```
Ser Thr Gln Thr Pro Ser Pro Pro Cys Gln Ala Phe Asn His Tyr Leu
        115             120             125

Ser Ala Met Ala Ser Met Arg Gln Ala Glu Pro Ala Asp Met Arg Pro
    130             135             140

Glu Ile Trp Ile Ala Gln Glu Leu Arg Arg Ile Gly Asp Glu Phe Asn
145             150             155             160

Ala Tyr Tyr Ala Arg Arg Val Phe Leu Asn Asn Tyr Gln Ala Ala Glu
            165             170             175

Asp His Pro Arg Met Val Ile Leu Arg Leu Leu Arg Tyr Ile Val Arg
            180             185             190

Leu Val Trp Arg Met His Gly Ser Gly Ala Gly Gly Ser Ala Gly Gly
            195             200             205

Ser Gly Ala Gly Ser Gly Ala Gly Ser Gly Ala His Ala Gly Arg Thr
    210             215             220

Gly Tyr Asp Asn Arg Glu Ile Val Met Lys Tyr Ile His Tyr Lys Leu
225             230             235             240

Ser Gln Arg Gly Tyr Glu Trp Asp Ala Gly Asp Val Gly Ala Ala Pro
            245             250             255

Pro Gly Ala Ala Pro Ala Pro Gly Ile Phe Ser Ser Gln Pro Gly His
            260             265             270

Thr Pro His Pro Ala Ala Ser Arg Asp Pro Val Ala Arg Thr Ser Pro
            275             280             285

Leu Gln Thr Pro Ala Ala Pro Gly Ala Ala Ala Gly Pro Ala Leu Ser
    290             295             300

Pro Val Pro Pro Val Val His Leu Thr Leu Arg Gln Ala Gly Asp Asp
305             310             315             320

Phe Ser Arg Arg Tyr Arg Arg Asp Phe Ala Glu Met Ser Ser Gln Leu
            325             330             335

His Leu Thr Pro Phe Thr Ala Arg Gly Arg Phe Ala Thr Val Val Glu
            340             345             350

Glu Leu Phe Arg Asp Gly Val Asn Trp Gly Arg Ile Val Ala Phe Phe
            355             360             365

Glu Phe Gly Gly Val Met Cys Val Glu Ser Val Asn Arg Glu Met Ser
    370             375             380

Pro Leu Val Asp Asn Ile Ala Leu Trp Met Thr Glu Tyr Leu Asn Arg
385             390             395             400

His Leu His Thr Trp Ile Gln Asp Asn Gly Gly Trp Asp Ala Phe Val
            405             410             415

Glu Leu Tyr Gly Pro Ser Met Arg Pro Leu Phe Asp Phe Ser Gly Gly
            420             425             430

Ser Trp Ser Gly Pro Gln Phe Glu Lys Gly
    435             440
```

<210> SEQ ID NO 2
<211> LENGTH: 441
<212> TYPE: PRT
<213> ORGANISM: Artificial Sequence
<220> FEATURE:
<223> OTHER INFORMATION: Fusion protein (BIM-Bcl-xL)

<400> SEQUENCE: 2

```
Gly Ala Lys Gln Pro Ser Asp Val Ser Ser Glu Cys Asp Arg Glu Gly
1               5               10              15

Arg Gln Leu Gln Pro Ala Glu Arg Pro Pro Gln Leu Arg Pro Gly Ala
        20              25              30
```

-continued

```
Pro Thr Ser Leu Gln Thr Glu Pro Gln Gly Asn Pro Glu Gly Asn His
        35              40              45

Gly Gly Glu Gly Asp Ser Cys Pro His Gly Ser Pro Gln Gly Pro Leu
    50              55              60

Ala Pro Pro Ala Ser Pro Gly Pro Phe Ala Thr Arg Ser Pro Leu Phe
65              70              75              80

Ile Phe Met Arg Arg Ser Ser Leu Leu Ser Arg Ser Ser Ser Gly Tyr
                85              90              95

Phe Ser Phe Asp Thr Asp Arg Ser Pro Ala Pro Met Ser Cys Asp Lys
                100             105             110

Ser Thr Gln Thr Pro Ser Pro Pro Cys Gln Ala Phe Asn His Tyr Leu
        115             120             125

Ser Ala Met Ala Ser Met Arg Gln Ala Glu Pro Ala Asp Met Arg Pro
    130             135             140

Glu Ile Trp Ile Ala Gln Glu Leu Arg Arg Ile Gly Asp Glu Phe Asn
145             150             155             160

Ala Tyr Tyr Ala Arg Arg Val Phe Leu Asn Asn Tyr Gln Ala Ala Glu
                165             170             175

Asp His Pro Arg Met Val Ile Leu Arg Leu Leu Arg Tyr Ile Val Arg
            180             185             190

Leu Val Trp Arg Met His Gly Ser Gly Ala Gly Gly Ser Ala Gly Gly
            195             200             205

Ser Gly Ala Gly Ser Gly Ala Gly Ser Gly Ser Gln Ser Asn Arg Glu
    210             215             220

Leu Val Val Asp Phe Leu Ser Tyr Lys Leu Ser Gln Lys Gly Tyr Ser
225             230             235             240

Trp Ser Gln Phe Ser Asp Val Glu Glu Asn Arg Thr Glu Ala Pro Glu
                245             250             255

Gly Thr Glu Ser Glu Met Glu Thr Pro Ser Ala Ile Asn Gly Asn Pro
            260             265             270

Ser Trp His Leu Ala Asp Ser Pro Ala Val Asn Gly Ala Thr Gly His
    275             280             285

Ser Ser Ser Leu Asp Ala Arg Glu Val Ile Pro Met Ala Ala Val Lys
    290             295             300

Gln Ala Leu Arg Glu Ala Gly Asp Glu Phe Glu Leu Arg Tyr Arg Arg
305             310             315             320

Ala Phe Ser Asp Leu Thr Ser Gln Leu His Ile Thr Pro Gly Thr Ala
                325             330             335

Tyr Gln Ser Phe Glu Gln Val Val Asn Glu Leu Phe Arg Asp Gly Val
                340             345             350

Asn Trp Gly Arg Ile Val Ala Phe Phe Ser Phe Gly Gly Ala Leu Cys
            355             360             365

Val Glu Ser Val Asp Lys Glu Met Gln Val Leu Val Ser Arg Ile Ala
    370             375             380

Ala Trp Met Ala Thr Tyr Leu Asn Asp His Leu Glu Pro Trp Ile Gln
385             390             395             400

Glu Asn Gly Gly Trp Asp Thr Phe Val Glu Leu Tyr Gly Asn Asn Ala
                405             410             415

Ala Ala Glu Ser Arg Lys Gly Gln Glu Arg Phe Asn Arg Gly Gly Ser
            420             425             430

Trp Ser Gly Pro Gln Phe Glu Lys Gly
            435             440
```

-continued

```
<210> SEQ ID NO 3
<211> LENGTH: 579
<212> TYPE: PRT
<213> ORGANISM: Artificial Sequence
<220> FEATURE:
<223> OTHER INFORMATION: Fusion protein (BIM-Mcl-1)

<400> SEQUENCE: 3

Gly Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Glu Gly Asn His
            35                  40                  45

Gly Gly Glu Gly Asp Ser Cys Pro His Gly Ser Pro Gln Gly Pro Leu
    50                  55                  60

Ala Pro Pro Ala Ser Pro Gly Pro Phe Ala Thr Arg Ser Pro Leu Phe
65                  70                  75                  80

Ile Phe Met Arg Arg Ser Ser Leu Leu Ser Arg Ser Ser Ser Gly Tyr
                85                  90                  95

Phe Ser Phe Asp Thr Asp Arg Ser Pro Ala Pro Met Ser Cys Asp Lys
            100                 105                 110

Ser Thr Gln Thr Pro Ser Pro Pro Cys Gln Ala Phe Asn His Tyr Leu
            115                 120                 125

Ser Ala Met Ala Ser Met Arg Gln Ala Glu Pro Ala Asp Met Arg Pro
    130                 135                 140

Glu Ile Trp Ile Ala Gln Glu Leu Arg Arg Ile Gly Asp Glu Phe Asn
145                 150                 155                 160

Ala Tyr Tyr Ala Arg Arg Val Phe Leu Asn Asn Tyr Gln Ala Ala Glu
                165                 170                 175

Asp His Pro Arg Met Val Ile Leu Arg Leu Leu Arg Tyr Ile Val Arg
            180                 185                 190

Leu Val Trp Arg Met His Gly Ser Gly Ala Gly Gly Ser Ala Gly Gly
            195                 200                 205

Ser Gly Ala Gly Ser Gly Ala Gly Ser Gly Phe Gly Leu Lys Arg Asn
    210                 215                 220

Ala Val Ile Gly Leu Asn Leu Tyr Cys Gly Gly Ala Gly Leu Gly Ala
225                 230                 235                 240

Gly Ser Gly Gly Ala Thr Arg Pro Gly Gly Arg Leu Leu Ala Thr Glu
                245                 250                 255

Lys Glu Ala Ser Ala Arg Arg Glu Ile Gly Gly Gly Glu Ala Gly Ala
            260                 265                 270

Val Ile Gly Gly Ser Ala Gly Ala Ser Pro Pro Ser Thr Leu Thr Pro
            275                 280                 285

Asp Ser Arg Arg Val Ala Arg Pro Pro Pro Ile Gly Ala Glu Val Pro
    290                 295                 300

Asp Val Thr Ala Thr Pro Ala Arg Leu Leu Phe Phe Ala Pro Thr Arg
305                 310                 315                 320

Arg Ala Ala Pro Leu Glu Glu Met Glu Ala Pro Ala Ala Asp Ala Ile
                325                 330                 335

Met Ser Pro Glu Glu Glu Leu Asp Gly Tyr Glu Pro Glu Pro Leu Gly
            340                 345                 350

Lys Arg Pro Ala Val Leu Pro Leu Leu Glu Leu Val Gly Glu Ser Gly
            355                 360                 365
```

-continued

```
Asn Asn Thr Ser Thr Asp Gly Ser Leu Pro Ser Thr Pro Pro Pro Ala
    370             375             380

Glu Glu Glu Glu Asp Glu Leu Tyr Arg Gln Ser Leu Glu Ile Ile Ser
385             390             395             400

Arg Tyr Leu Arg Glu Gln Ala Thr Gly Ala Lys Asp Thr Lys Pro Met
            405             410             415

Gly Arg Ser Gly Ala Thr Ser Arg Lys Ala Leu Glu Thr Leu Arg Arg
            420             425             430

Val Gly Asp Gly Val Gln Arg Asn His Glu Thr Ala Phe Gln Gly Met
            435             440             445

Leu Arg Lys Leu Asp Ile Lys Asn Glu Asp Asp Val Lys Ser Leu Ser
    450             455             460

Arg Val Met Ile His Val Phe Ser Asp Gly Val Thr Asn Trp Gly Arg
465             470             475             480

Ile Val Thr Leu Ile Ser Phe Gly Ala Phe Val Ala Lys His Leu Lys
            485             490             495

Thr Ile Asn Gln Glu Ser Cys Ile Glu Pro Leu Ala Glu Ser Ile Thr
            500             505             510

Asp Val Leu Val Arg Thr Lys Arg Asp Trp Leu Val Lys Gln Arg Gly
            515             520             525

Trp Asp Gly Phe Val Glu Phe Phe His Val Glu Asp Leu Glu Gly Gly
            530             535             540

Ile Arg Asn Val Leu Leu Ala Phe Ala Gly Val Ala Gly Val Gly Ala
545             550             555             560

Gly Leu Ala Tyr Leu Ile Arg Gly Gly Ser Trp Ser Gly Pro Gln Phe
            565             570             575

Glu Lys Gly

<210> SEQ ID NO 4
<211> LENGTH: 383
<212> TYPE: PRT
<213> ORGANISM: Artificial Sequence
<220> FEATURE:
<223> OTHER INFORMATION: Fusion protein (BAX-BAK)

<400> SEQUENCE: 4

Gly Ala Ser Gly Gln Gly Pro Gly Pro Pro Arg Gln Glu Cys Gly Glu
1               5               10              15

Pro Ala Leu Pro Ser Ala Ser Glu Glu Gln Val Ala Gln Asp Thr Glu
            20              25              30

Glu Val Phe Arg Ser Tyr Val Phe Tyr Arg His Gln Gln Glu Gln Glu
            35              40              45

Ala Glu Gly Val Ala Ala Pro Ala Asp Pro Glu Met Val Thr Leu Pro
    50              55              60

Leu Gln Pro Ser Ser Thr Met Gly Gln Val Gly Arg Gln Leu Ala Ile
65              70              75              80

Ile Gly Asp Asp Ile Asn Arg Arg Tyr Asp Ser Glu Phe Gln Thr Met
            85              90              95

Leu Gln His Leu Gln Pro Thr Ala Glu Asn Ala Tyr Glu Tyr Phe Thr
            100             105             110

Lys Ile Ala Thr Ser Leu Phe Glu Ser Gly Ile Asn Trp Gly Arg Val
            115             120             125

Val Ala Leu Leu Gly Phe Gly Tyr Arg Leu Ala Leu His Val Tyr Gln
            130             135             140

His Gly Leu Thr Gly Phe Leu Gly Gln Val Thr Arg Phe Val Val Asp
```

-continued

```
145                150                155                160

Phe Met Leu His His Cys Ile Ala Arg Trp Ile Ala Gln Arg Gly Gly
                165                170                175

Trp Val Ala Ala Leu Asn Leu Gly Asn Gly Ser Gly Ala Gly Gly Ser
            180                185                190

Ala Gly Gly Ser Gly Ala Gly Ser Gly Ala Gly Ser Gly Asp Gly Ser
            195                200                205

Gly Glu Gln Pro Arg Gly Gly Gly Pro Thr Ser Ser Glu Gln Ile Met
    210                215                220

Lys Thr Gly Ala Leu Leu Leu Gln Gly Phe Ile Gln Asp Arg Ala Gly
225                230                235                240

Arg Met Gly Gly Glu Ala Pro Glu Leu Ala Leu Asp Pro Val Pro Gln
            245                250                255

Asp Ala Ser Thr Lys Lys Leu Ser Glu Cys Leu Lys Arg Ile Gly Asp
            260                265                270

Glu Leu Asp Ser Asn Met Glu Leu Gln Arg Met Ile Ala Ala Val Asp
            275                280                285

Thr Asp Ser Pro Arg Glu Val Phe Phe Arg Val Ala Ala Asp Met Phe
    290                295                300

Ser Asp Gly Asn Phe Asn Trp Gly Arg Val Val Ala Leu Phe Tyr Phe
305                310                315                320

Ala Ser Lys Leu Val Leu Lys Ala Leu Cys Thr Lys Val Pro Glu Leu
            325                330                335

Ile Arg Thr Ile Met Gly Trp Thr Leu Asp Phe Leu Arg Glu Arg Leu
            340                345                350

Leu Gly Trp Ile Gln Asp Gln Gly Gly Trp Asp Gly Leu Leu Ser Tyr
            355                360                365

Phe Gly Thr Gly Gly Ser Trp Ser Gly Pro Gln Phe Glu Lys Gly
    370                375                380

<210> SEQ ID NO 5
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 5

Gly Ser Gly Ala Gly Gly Ser Ala Gly Gly Ser Gly Ala Gly Ser Gly
1               5                10                15

Ala Gly Ser Gly
            20
```